United States Patent
Shui et al.

(10) Patent No.: US 10,305,520 B2
(45) Date of Patent: May 28, 2019

(54) REMOVING RF INTERFERENCE THROUGH SCAN RATE LOCKING

(71) Applicant: Apple Inc., Cupertino, CA (US)

(72) Inventors: Tao Shui, Cupertino, CA (US); Brian R. Land, Woodside, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 15/607,029

(22) Filed: May 26, 2017

(65) Prior Publication Data

US 2017/0346511 A1    Nov. 30, 2017

Related U.S. Application Data

(60) Provisional application No. 62/342,386, filed on May 27, 2016.

(51) Int. Cl.
*A61B 5/00* (2006.01)
*H04B 1/04* (2006.01)
*H04B 1/3827* (2015.01)

(52) U.S. Cl.
CPC ........... *H04B 1/0475* (2013.01); *A61B 5/00* (2013.01); *H04B 2001/0491* (2013.01); *H04B 2001/3855* (2013.01); *H04B 2001/3861* (2013.01)

(58) Field of Classification Search
CPC ........ G06F 2203/04106; G06F 3/0416; H04B 1/0475; H04B 2001/0491
See application file for complete search history.

(56) References Cited

U.S. PATENT DOCUMENTS

| | | | |
|---|---|---|---|
| 5,483,261 A | 1/1996 | Yasutake | |
| 5,488,204 A | 1/1996 | Mead et al. | |
| 5,825,352 A | 10/1998 | Bisset et al. | |
| 5,835,079 A | 11/1998 | Shieh | |

(Continued)

FOREIGN PATENT DOCUMENTS

| | | | |
|---|---|---|---|
| JP | 2000-163031 A | 6/2000 | |
| JP | 2002-342033 A | 11/2002 | |

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

(Continued)

*Primary Examiner* — Khanh C Tran
(74) *Attorney, Agent, or Firm* — Morrison & Foerster LLP

(57) ABSTRACT

This relates to methods and apparatus for mitigating effects of the presence of RF communication signals. In some examples, non-linearity and rectification of the RF communication signals can become rectified in sensor circuitry such that spectral components of a frame or sub-frame timing of the RF communication signals can be aliased into the sensor circuitry output within a bandwidth of interest. In some examples, a notch filter can be employed to remove the aliased RF communication signals from the sensor output. In some examples, a sampling rate used for sampling the user's physiological signals can be generated such that the sampling of the sensor is synchronous with the RF communication signals. In some examples, the sampling rate for the sensor can be generated as an integer multiple or integer submultiple of the frame or sub-frame timing of the RF communication signals.

21 Claims, 15 Drawing Sheets

(56) References Cited

U.S. PATENT DOCUMENTS

| | | | |
|---|---|---|---|
| 5,880,411 | A | 3/1999 | Gillespie et al. |
| 6,188,391 | B1 | 2/2001 | Seely et al. |
| 6,310,610 | B1 | 10/2001 | Beaton et al. |
| 6,323,846 | B1 | 11/2001 | Westerman et al. |
| 6,411,250 | B1 * | 6/2002 | Oswald .................. G01S 7/023 |
| | | | 342/101 |
| 6,473,008 | B2 | 10/2002 | Auerbach et al. |
| 6,690,387 | B2 | 2/2004 | Zimmerman et al. |
| 7,015,894 | B2 | 3/2006 | Morohoshi |
| 7,076,403 | B2 | 9/2006 | Tice |
| 7,184,064 | B2 | 2/2007 | Zimmerman et al. |
| 7,663,607 | B2 | 2/2010 | Hotelling et al. |
| 7,812,750 | B2 | 10/2010 | Laksawala et al. |
| 7,821,437 | B1 | 10/2010 | Rud et al. |
| 7,847,716 | B2 | 12/2010 | Rivoir |
| 8,479,122 | B2 | 7/2013 | Hotelling et al. |
| 2006/0197753 | A1 | 9/2006 | Hotelling |
| 2011/0058485 | A1 * | 3/2011 | Sloan ................. G06F 19/3418 |
| | | | 370/242 |
| 2012/0214422 | A1 * | 8/2012 | Shi ....................... H04B 1/3838 |
| | | | 455/67.11 |
| 2014/0290368 | A1 * | 10/2014 | Guo ....................... G01N 29/04 |
| | | | 73/602 |
| 2018/0081030 | A1 * | 3/2018 | McMahon ........... A61B 5/0507 |

OTHER PUBLICATIONS

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

* cited by examiner

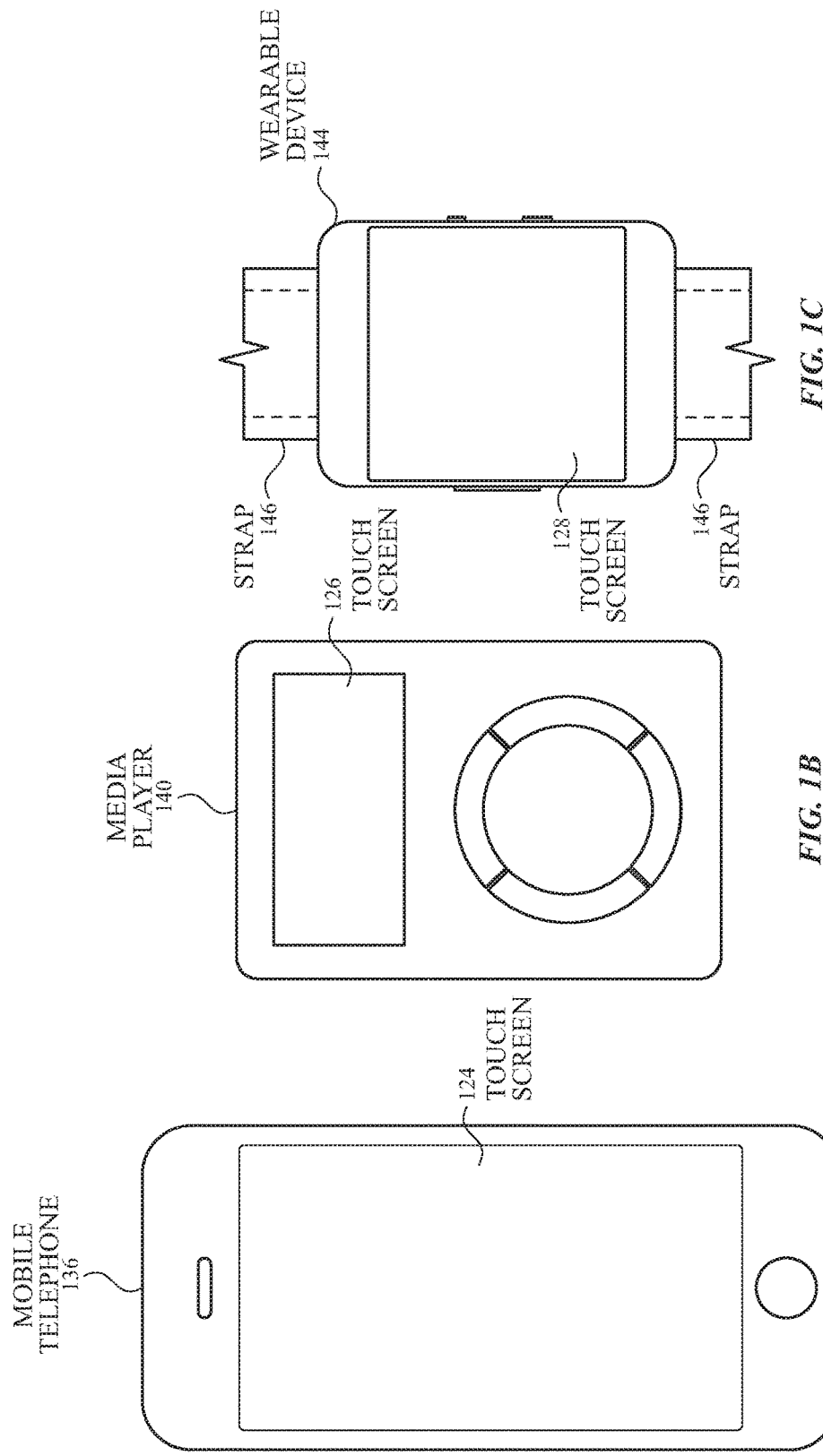

REMOVING RF INTERFERENCE THROUGH SCAN RATE LOCKING

CROSS-REFERENCE TO RELATED APPLICATIONS

This application claims priority to U.S. Provisional Patent Application Ser. No. 62/342,386, filed May 27, 2016, which is hereby incorporated by reference in its entirety.

FIELD OF THE DISCLOSURE

This relates generally to scan rate adjustment, and more particularly to adjusting scan rates of sensors in proximity to radio frequency communication circuitry.

BACKGROUND OF THE DISCLOSURE

A photoplethysmogram (PPG) signal can be measured by PPG systems to derive corresponding physiological signals (e.g., pulse rate). In a basic form, PPG systems can employ a light source or light emitter that emits light through an aperture into the user's tissue. In addition, a light detector can be included to receive light through an aperture that reflects off and exits the tissue. However, determination of the user's physiological signals can be erroneous due to variations in the user's skin type, usage conditions, and environmental conditions affecting the signal of the reflected light. Radio Frequency (RF) circuitry can be located in proximity to sensors such as the light detectors of PPG systems, and the RF communication signals from the RF circuitry can interfere with the operation of the sensors by injecting noise into the sensor signals.

SUMMARY OF THE DISCLOSURE

This relates to methods and apparatus for mitigating effects of the presence of RF communication signals. The user's physiological signals can be measured with one or more light emitters and one or more light sensors. In some examples, non-linearity and rectification of the RF communication signals can become rectified in the sensor circuitry such that spectral components of a frame or sub-frame timing of the RF communication signals can be aliased into the sensor circuitry output within a bandwidth of interest. In some examples, a notch filter can be employed to remove the aliased RF communication signals from the sensor output. In some examples, a sampling rate used for sampling the user's physiological signals can be generated such that the sampling of the sensor is synchronous with the RF communication signals. In some examples, the sampling rate for the sensor can be generated as an integer multiple or integer submultiple of the frame or sub-frame timing of the RF communication signals. In some examples, sampling at the synchronized sample rate can move the aliased RF communication signals out of the bandwidth of interest of the sensor outputs. In some examples, sampling at the synchronized sample rate can move the aliased RF communication signals to DC (i.e., frequency=0).

BRIEF DESCRIPTION OF THE DRAWINGS

FIGS. 1A-1C illustrate systems in which examples of the disclosure can be implemented.

DETAILED DESCRIPTION

Figure 2A:
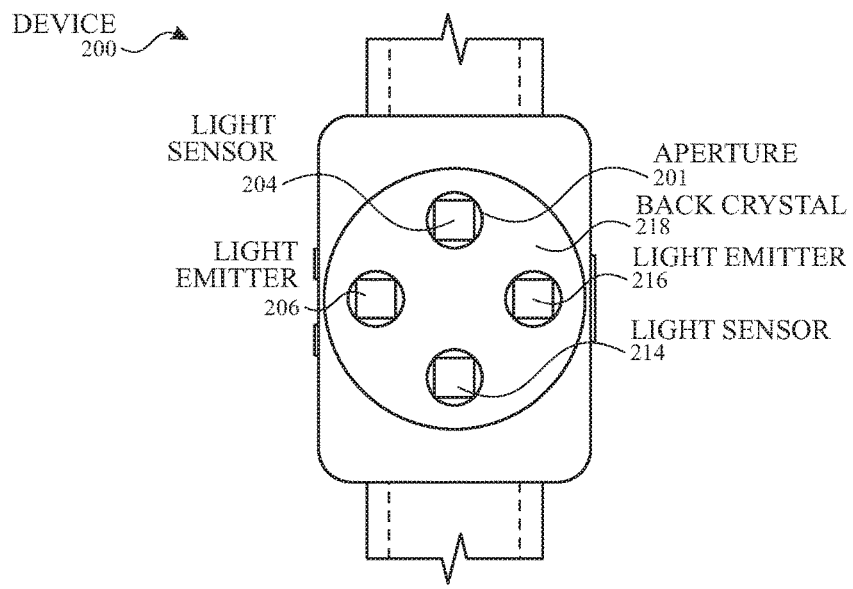
FIG. 2A illustrates a top view of an exemplary electronic device including light sensors and light emitters for measuring a PPG signal according to examples of the disclosure.

A photoplethysmographic (PPG) signal can be measured by PPG systems to derive corresponding physiological signals (e.g., pulse rate). Such PPG systems can be designed to be sensitive to changes in a user's tissue that can result from fluctuations in the amount or volume of blood or blood oxygen in the vasculature of the user. In a basic form, PPG systems can employ a light source or light emitter that emits light through an aperture into the user's tissue, and a light sensor to receive light that reflects and/or scatters and exits the tissue through another aperture. The PPG signal is the amplitude of reflected and/or scattered light that is modulated with volumetric change in blood volume in the tissue. However, in some examples, some of the reflected and/or scattered light can be lost, leading to a PPG signal measured by the light sensor having a low signal strength. Additionally, the PPG signal can be distorted by noise due to artifacts. Artifacts can result from, for example, the user's movement or ambient light intrusion that can saturate or degrade the signal by introducing noise into the signal. As a result, it can be difficult to accurately determine the user's physiological state.

This relates methods and apparatus for mitigating effects of the presence of RF communication signals. The user's physiological signals can be measured with one or more light emitters and one or more light sensors. In some examples, non-linearity and rectification of the RF communication signals can become rectified in the sensor circuitry such that spectral components of a frame or sub-frame timing of the RF communication signals can be aliased into the sensor circuitry output within a bandwidth of interest. In some examples, a notch filter can be employed to remove the aliased RF communication signals from the sensor output. In some examples, a sampling rate used for sampling the user's physiological signals can be generated such that the sampling of the sensor is synchronous with the RF communication signals. In some examples, the sampling rate for the sensor can be generated as an integer multiple or integer submultiple of the frame or sub-frame timing of the RF communication signals. In some examples, sampling at the synchronized sample rate can move the aliased RF communication signals out of the bandwidth of interest of the sensor outputs. In some examples, sampling at the synchronized sample rate can move the aliased RF communication signals to DC (i.e., frequency=0). Examples for mitigating the effects of the presence of RF communication signals will be discussed in further detail with regards to FIG. 9 below.

In the following description of examples, reference is made to the accompanying drawings in which it is shown by way of illustration specific examples that can be practiced. It is to be understood that other examples can be used and structural changes can be made without departing from the scope of the various examples. Numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well-known process steps and/or structures have not been described in detail in order to not obscure some of the aspects and/or features described or referenced herein.

FIGS. 1A-1C illustrate systems in which examples of the disclosure can be implemented. FIG. 1A illustrates an exemplary mobile telephone 136 that can include a touch screen 124. FIG. 1B illustrates an exemplary media player 140 that can include a touch screen 126. FIG. 1C illustrates an exemplary wearable device 144 that can include a touch screen 128 and can be attached to a user using a strap 146. The systems of FIGS. 1A-1C can utilize scan rate locking for removing radio frequency interference from a PPG signal (or other similar sensor signal) as will be disclosed.

Figure 2B:
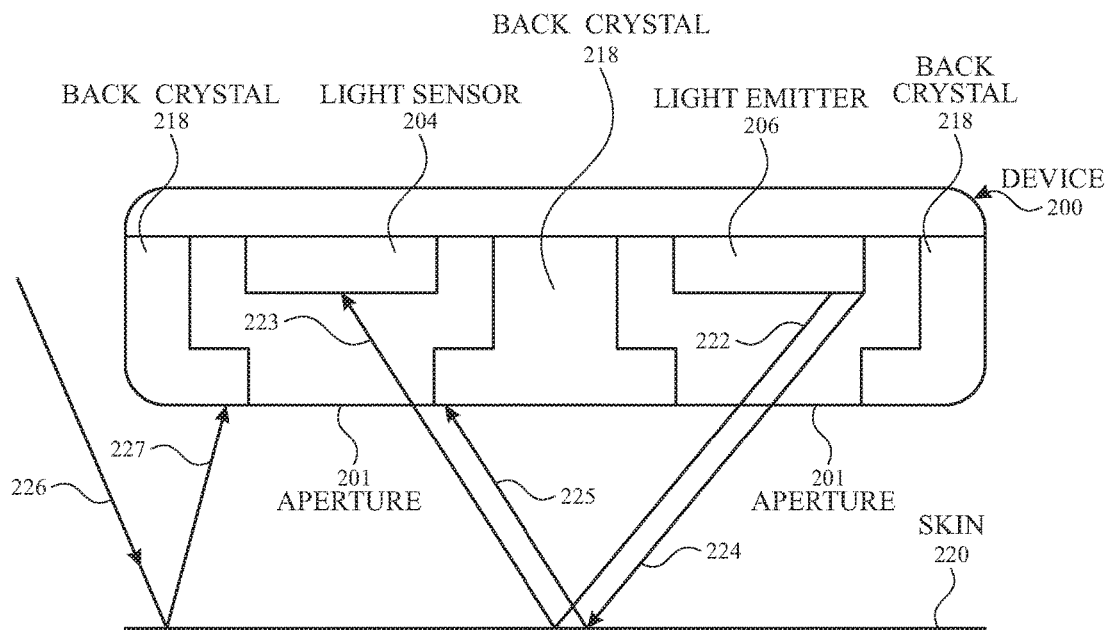
FIG. 2B illustrates a cross-sectional view of an exemplary electronic device including light sensors and light emitters for measuring a PPG signal according to examples of the disclosure.

FIG. 2A illustrates a top view and FIG. 2B illustrates a cross-sectional view of an exemplary electronic device including light sensors and light emitters for measuring a PPG signal according to examples of the disclosure. The top view in FIG. 2A can be viewed as the underside of wearable device 144 of FIG. 1C, for example. A light sensor 204 can be located proximate to a light emitter 206 on a surface of device 200. Additionally, another light sensor 214 can be located or paired with light emitter 216 on a surface of device 200. Device 200 can be situated such that light sensors 204 and 214 and light emitters 206 and 216 are proximate to a skin 220 of a user. For example, device 200 can be held in a user's hand or strapped to a user's wrist, among other possibilities.

Light emitter 206 can generate light 222 and 224 exiting aperture 201. Light 222 can be directed towards, and incident upon, the user's skin 220. A portion of light 222 can be absorbed by skin 220, vasculature, and/or blood, and a portion of light (i.e., light 223) can reflect back for detection by light sensor 204. Light 224 can also be incident upon skin 220, a portion of light 224 can be absorbed by skin 220, vasculature, and/or blood, and a portion of light (i.e., light 225) can reflect back towards device 200. However, light 225 can be incident on back crystal 218 and may not reach light sensor 204. Similarly, ambient light 226 can be incident upon skin 220. A portion of the ambient light (i.e., light 227) can reflect back towards device 200, and light 227 can be absorbed by back crystal 218.

Figure 2C:
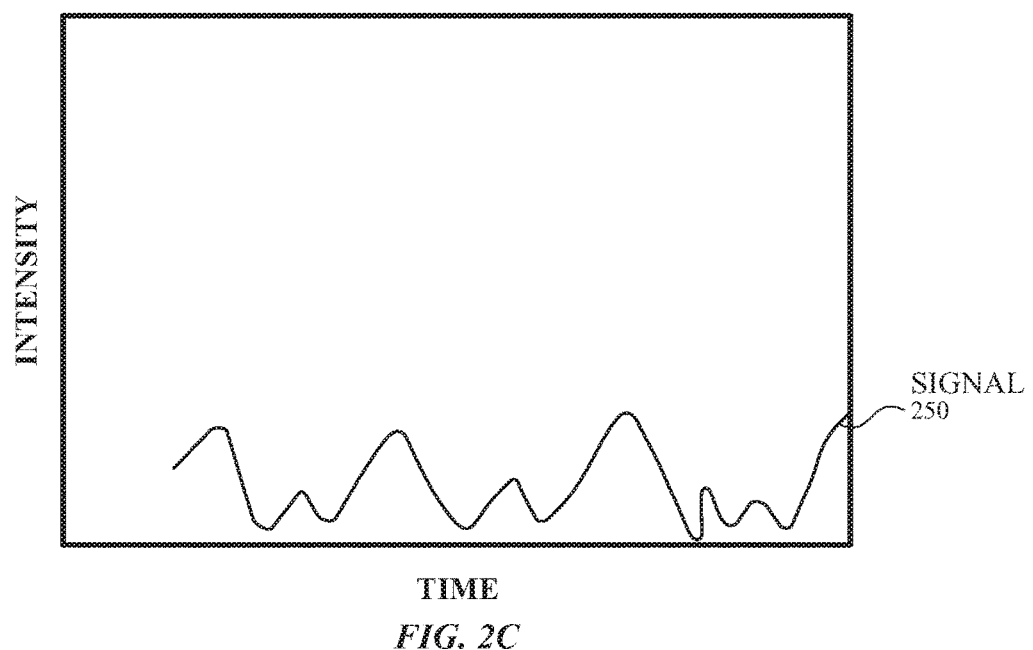
FIG. 2C illustrates a signal detected by a light sensor in PPG system according to examples of the disclosure.

FIG. 2C illustrates an exemplary signal detected by a light sensor for determining the user's physiological state in an exemplary electronic device according to examples of the disclosure. Signal 250 can be a low intensity signal measured by light sensor 204. While the intensity of the detected signal 250 can be increased by increasing the intensity of light generated from light emitter 206, such a solution may not be feasible especially in portable or compact-sized electronic devices, whose power consumption can be limited due to portability and size requirements.

Figure 3:
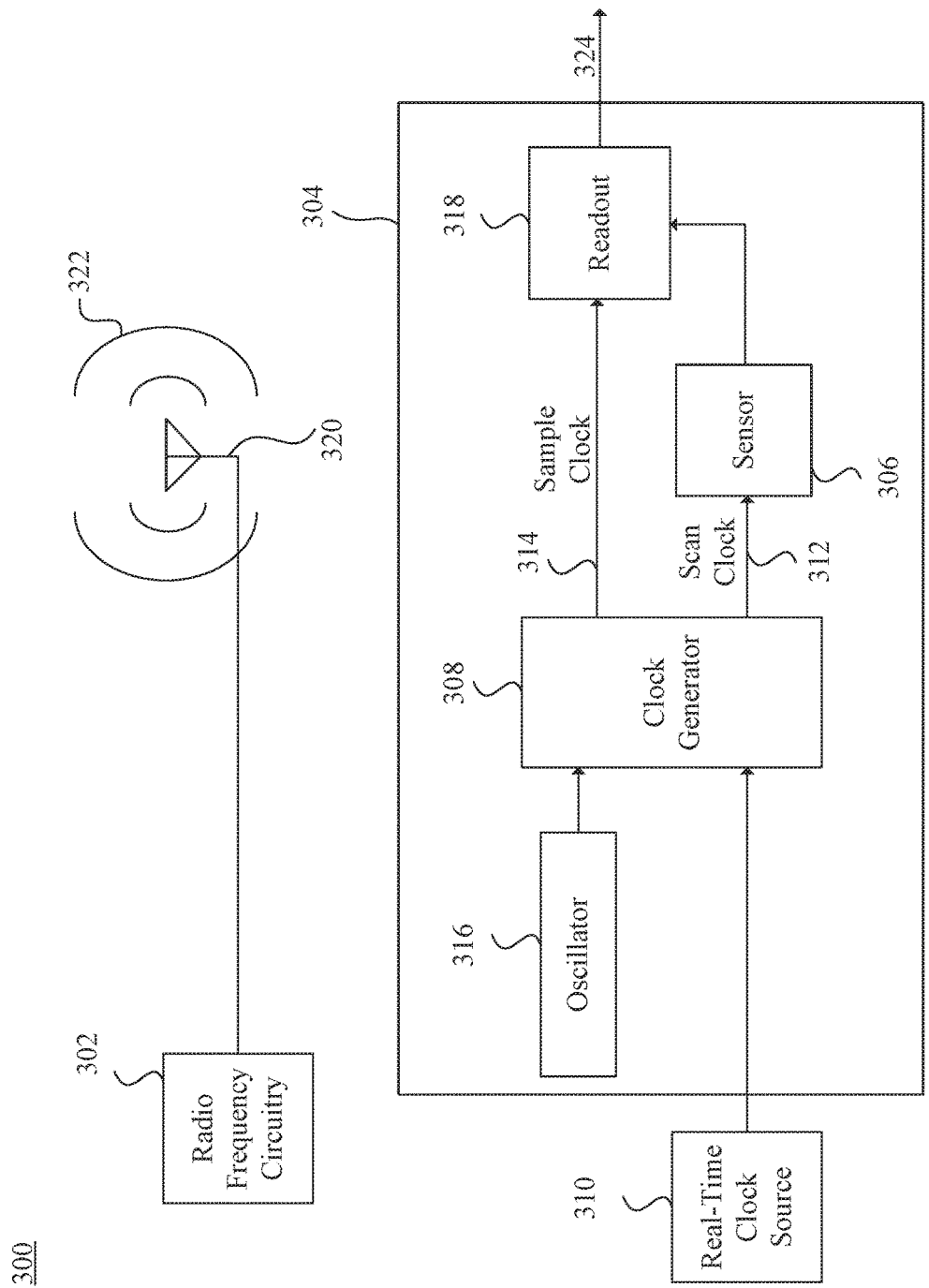
FIG. 3 illustrates a block diagram of an exemplary device including radio frequency circuitry and precision sensor circuitry according to examples of the disclosure.

FIG. 3 illustrates a block diagram of an exemplary device 300 including radio frequency circuitry 302 and precision sensor circuitry 304 (which can include PPG sensor circuitry described above) according to examples of the disclosure. The exemplary device 300 illustrates one possible configuration that may exhibit radio frequency interference (e.g., RF cross-talk) with sensor circuitry. It should be understood that other configurations can result in radio frequency interference, and the principles described herein can be applied analogously. In some examples, the precision sensor circuitry 304 can include a sensor 306 (which can correspond to light sensors 204/214 above) that can be provided a scan clock 312 for controlling timing of sensing operations of the sensor. In some examples, a clock generator 308 can generate the scan clock 312, as well as other clock signals such as a sample clock 314. In some examples, the clock generator can include one or more divide by N clock generators for generating clocks of different desired output clock frequencies based on reference input clock sources. In some examples, clock generator 308 can receive an input from a real-time clock (RTC) source 310, and the RTC source 310 can produce an RTC clock signal 311 operating at a frequency $f_{RTC}$ (which can be nominally equal to 32.768 kHz for a standard RTC source). In some examples, the scan clock 312 can be generated by dividing (e.g., with one of the divide by N clock generators in the clock generator 308) the RTC source 310 frequency by a factor $N_1$ (e.g., $N_1$=128) to produce the scan clock 312 having frequency $f_{scan}=f_{RTC}/N_1$ (e.g., 32.768 kHz/128=256 Hz). In some examples, the scan clock 312 can provide the timing base for performing sensing operations at sensor 306. In some examples, an additional reference clock source, such as oscillator 316 (e.g., a crystal oscillator) can be provided to the clock generator 308 as a reference for clock signals belonging to a separate clocking domain from the scan clock 312. In some examples, sensor 306 output data can be processed in readout circuitry 318 (e.g., with filters, analog-to-digital converters (ADCs), etc.) to produce output signals indicative of the desired data (e.g., output signals that can be used to derive physiological signals). In some examples, sample clock 314 can be utilized as a clock for readout circuitry 318, for example providing a clock for an ADC used for converting analog sensor 306 output signals into digital signals 324 for further processing (e.g., for analyzing detected PPG signals to determine a user's heart rate).

In some examples, radio frequency (RF) circuitry 302 can be used to transmit and receive RF communication signals 322 via an antenna 320 connected to the radio frequency circuitry. The RF communication signals 322 can be used for communication over a communication network (e.g., cellular, LTE, etc.) and/or for direct device-to-device communication with other nearby devices. In some examples, the RF communication signals 322 can become coupled into the sensor 306 (e.g., through routing traces in the sensor circuitry), thus introducing noise into the sensor data. In some examples, the RF circuitry 302 can generate RF communication signals 322 at a carrier frequency that is many orders of magnitude higher than $f_{scan}$ (e.g., LTE can operate with carrier frequencies ranging from 700 to 2600 MHz depending on region). In some examples, the RF communication signals can be asynchronous to other clock sources of the device such as the oscillator 316 and RTC source 310. In some examples, the RF communication signals 322 can be present in output of the sensors 306 in a phenomenon referred to as RF interference (RFI). In some examples, rectification and sampling of the RF communication signals 322 by the precision sensor circuitry 304 can result in in-band noise. For example, a particular sensor 306 can have desired output signals that fall within a bandwidth of interest $B_{sense}$ (e.g., between a low frequency $f_L$, e.g., 1 Hz and a high frequency $f_H$, e.g. 10 Hz) and RFI from the RF communication signals 322 can result in spurious signals (e.g., due to aliasing) within $B_{sense}$. The resulting in-band sensor noise can interfere with the ability to properly detect the sensor 306 output. The mechanism for how the much higher frequency RF communication signals 322 ends up within the bandwidth of interest $B_{sense}$ will be explained in further detail below. As will be explained in more detail below, examples of the disclosure are directed to eliminating the effects of the RFI caused by the RF communication signals 322 within the bandwidth of interest of the sensor 306 data.

While the example above illustrates multiple reference clock sources, in some examples (not shown), a single reference clock source, e.g., one of the RTC source 310 or oscillator 316, can be used as the reference for generating all of the clock generator 308 output clocks, e.g., scan clock 312 and sample clock 314. An advantage of using a single reference clock source can be reduced power consumption due to operating only one reference clock rather than expending additional power to operate multiple reference clocks. An advantage to providing separate references to the clock generator 308 is increased flexibility to change characteristics of individual clock generator outputs without affecting others. Exemplary techniques for addressing the radio frequency interferences described in FIGS. 3-8 will be described in more detail below with respect to FIG. 9.

Figure 4:
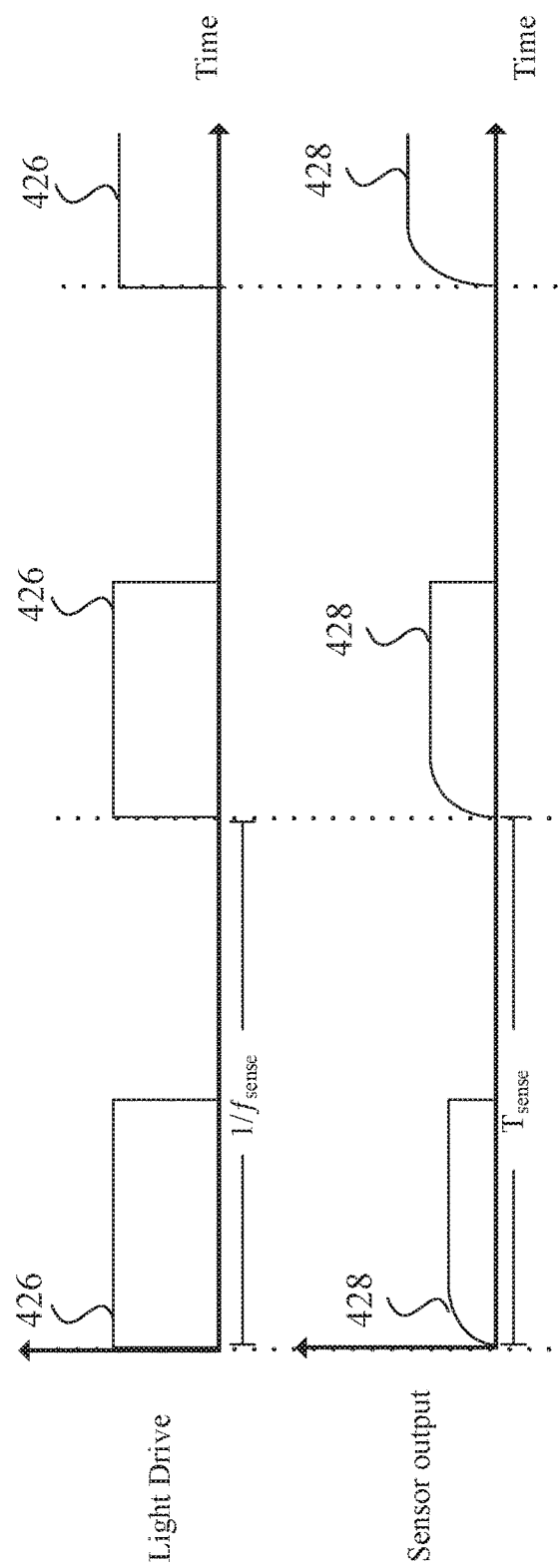
FIG. 4 illustrates an exemplary timing diagram of an exemplary sensor operation according to examples of the disclosure.
Figure 5:
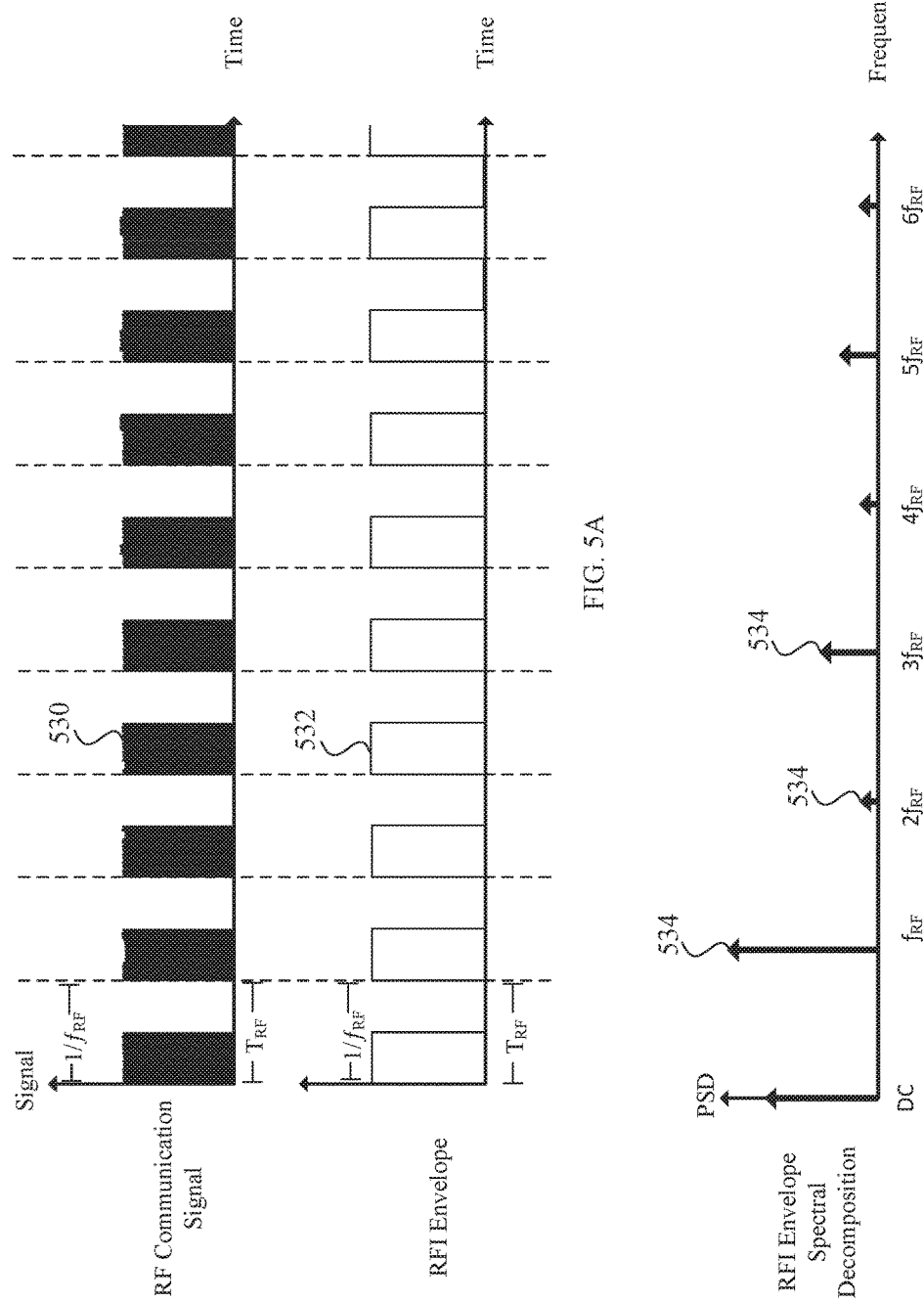
FIGS. 5A-5B illustrate exemplary timing signals and spectral characteristics of radio frequency interference that can result from RF communication signals according to examples of the disclosure.

FIG. 4 illustrates an exemplary timing diagram of an exemplary sensor operation (which can correspond to sensor 306 above) according to examples of the disclosure. In some examples, the sensor 306 can be part of a PPG system made up of light transmitters and light sensors. As explained above, the transmitter can be stimulated to emit light, for example as represented by a high level 426 of the emit light signal (e.g., a signal driving an LED). In some examples, light that reflects and/or scatters from a user's tissue can be detected by light sensors, which can convert the received light into electrical signals. Sensor outputs 428 illustrate exemplary outputs of a light sensor, which can be modulated, for example, based on volumetric change in blood volume in tissue. In some examples, the sensor outputs 428 can have a settling time (e.g., as illustrated by upward ramp of the sensor outputs during each scan period) during which the sensor output data can be ignored and/or discarded. In some examples, the sensor outputs can be sampled by an ADC (e.g., an ADC included in readout circuitry 318 above) that can sample the sensor output multiple times during a single scan cycle. The repeating pattern of emitting and sensing light can occur at a regular frequency $f_{sense}$ and can have an associated scan period $T_{sense}$. In some examples, the scan period can be generated from the clock generator 308 illustrated above, which can ultimately be derived from the RTC source 310 above.

FIGS. 5A-5B illustrate exemplary timing signals and spectral characteristics of radio frequency interference that can result from RF communication signals 530 (which can correspond to RF communication signals 322 above) according to examples of the disclosure. In some examples, as illustrated above in FIG. 3, a device can include RF circuitry 302 for transmitting and receiving radio frequency communication signals 530. In some examples, the RF circuitry can operate at a carrier frequency that is multiple orders of magnitude greater than the scan frequency $f_{scan}$ of sensor circuitry also included in the device (e.g., LTE can operate with carrier frequencies ranging from 700 to 2600 MHz depending on region). In some examples, The RF communication signal 530 can be broken into multiple "frames" and/or "sub-frames" of communication, which can each have a defined length of time. For example, some LTE communications protocols include frames lasting 10 ms with sub-frames lasting 1 ms each. FIG. 5A illustrates an exemplary communication protocol having sub-frames with a period $T_{RF}$ (e.g., 1 ms in the case of LTE) and an associated sub-frame frequency $f_{RF}$ (e.g., 1 kHz in the case of LTE). During these sub-frames, RF communication signals 530 can actively transmit during some or all of the sub-frame period $T_{RF}$. In some examples, due to non-linearity and/or rectification caused by analog circuitry (e.g., within precision sensor circuitry 304 in FIG. 3 above) that can be physically nearby the RF antenna (e.g., 320 above), an envelope 532 of the RF communication signal can appear in the output of the sensor circuitry 306. In other words, the very high frequency communications signals 530 can appear as a lower frequency RFI envelope signal in the sensor output. In the illustrated example, RF communication signals 530 are illustrated as active during approximately the first half of the sub-frame period $T_{RF}$ while being inactive during the second half of the sub-frame period. Accordingly, the RFI envelope 532 of the RF communication signal 530 can be approximated as a square wave having a period of $T_{RF}$. Because RF communication signals 530 can require large amounts of power to communicate with distant communication networks, the RFI 532 resulting from the RF communication signals can also be significant. The RFI 532 can interfere with the sensor operation, particularly for sensors where sensor output signal amplitudes can be small and signal-to-noise ratio (SNR) margins for resolving the sensor output signals can be low.

FIG. 5B illustrates an exemplary frequency domain representation of the RFI envelope 532 illustrated in FIG. 5A. According to Fourier Analysis, any periodic RFI envelope signal can be represented as a sum of sinusoids (or tones). For a square wave (e.g., as depicted for the RFI envelope 532), the signal can be represented as a sum of a sinusoid at frequency $f_{RF}$ (e.g., 1 khz corresponding to a 1 ms sub-frame interval in some LTE modes) and sinusoids at harmonics of $f_{RF}$ (e.g., $2f_{RF}$, $3f_{RF}$, $4f_{RF}$, etc.) For an ideal square wave, the fundamental component (e.g., at $f_{RF}$) can have the largest value, and the remaining components can be odd numbered harmonics (e.g., $3f_{RF}$, $5f_{RF}$, etc.). For the ideal square wave, the even harmonic components can be zero. However, because the RFI envelope 532 depicted in FIG. 5A can be the result of non-linearity effects and rectification of the RF communication signal (which can include varied data between successive sub-frames), a perfect square wave RFI envelope is not expected. Thus, the RFI envelope spectral decomposition illustrated in FIG. 5B also includes non-zero values even harmonics (e.g., $2f_{RF}$, $4f_{RF}$). As discussed above, the RF communication signal 530 can be completely asynchronous with an RTC source (e.g., 310 above) that can provide a time-base for operations of sensor 306 above. As will be described further below, sampling of a sensor (e.g., sensor 306 above) in proximity to the RF communication signals operating on different clock domains can result in the RFI signal 532 appearing as noise within a bandwidth of interest $B_{sense}$ of the sensor output signal, which can interfere with correctly resolving desired signals (e.g., PPG signals) from the sensor output data.

While the RFI envelope 532 is illustrated above as a square wave, it should be understood by those of skill in the art that in practice the RF communication signals 530 can have different characteristics that will result in a different RFI envelope 532. However, to the extent that the RF communication signal is broken into sub-frames (or frames) having a period $T_{RF}$, a frequency domain representation of the RFI envelope is still likely to include tones at the associated frequency $f_{RF}$ and its harmonics. Thus, while the relative amplitudes of the various RFI envelope 532 frequency components 534 are likely to change, the frequency domain representation of the RFI envelope is likely to contain components at the same frequencies even with significantly different RF communication signal 530 characteristics. Accordingly, the principles described below for removing the RF Interference can be applied to the general case according to the principles and examples described in the disclosure.

Figure 6:
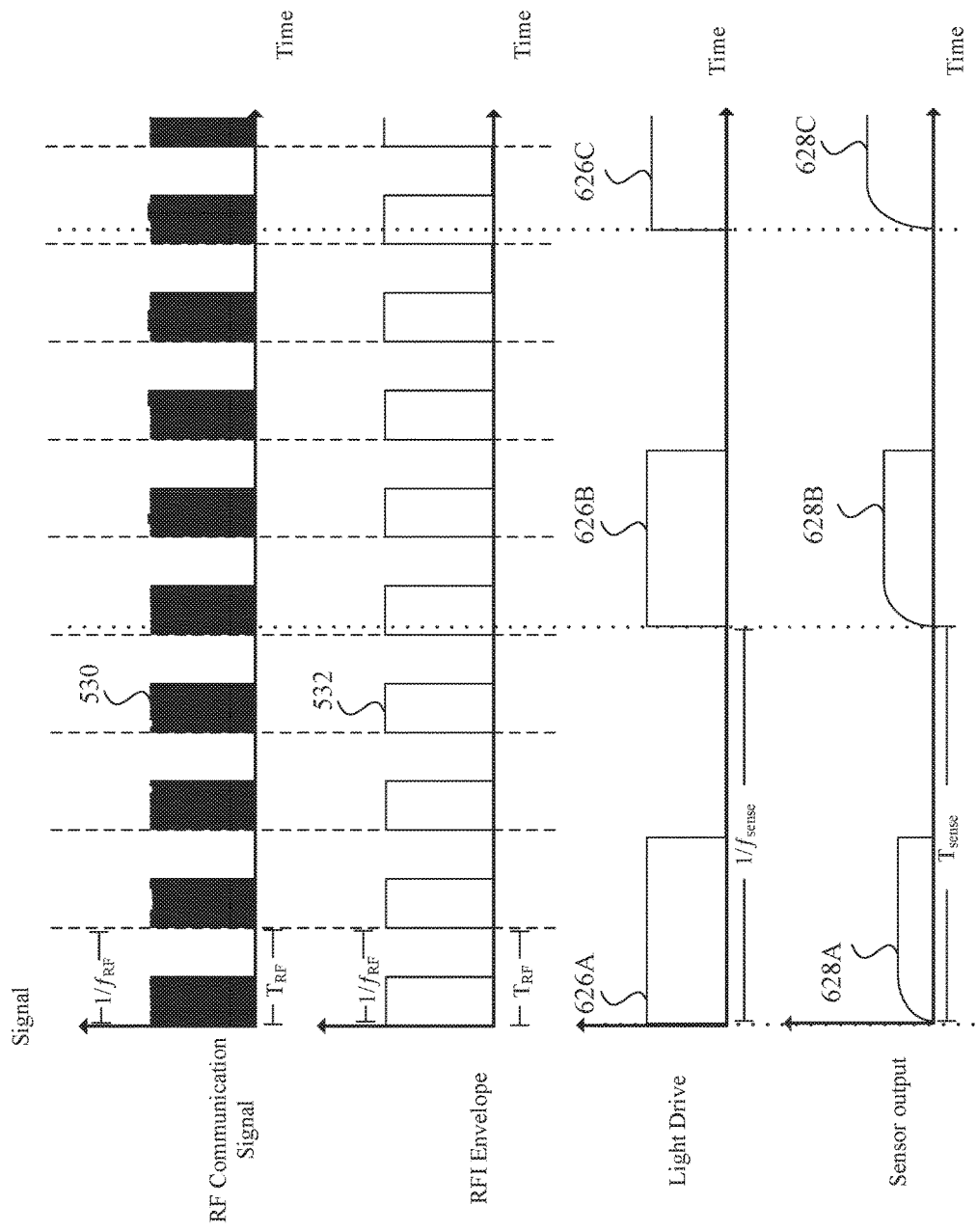
FIG. 6 illustrates timings of RF communication signals and sensor signals that can result from asynchronous clocking according to examples of the disclosure.

FIG. 6 illustrates timings of RF communication signals 530 and sensor signals (626A-626C and 628A-626C) that can result from asynchronous clocking according to examples of the disclosure. In some examples, the RF communication signals 530 can have an associated periodic RFI envelope 532 having an RF frame timing period $T_{RF}$ (e.g., a period of frames or sub-frames) as described above. In some examples, sensor circuitry (e.g., from sensor 306 above) can have a scan period of $T_{sense}$ that can be generated asynchronously to the RF frame timing. As can be seen in FIG. 6, while the beginning of sensor scan sequence 626A can begin aligned with the beginning of one RF communication signal 530 sub-frame (or frame), the following sensor scan 626B (and the beginning of subsequent sensor scans, e.g., 626C) can be out of alignment with the beginning sub-frames (or frames) of the RF communication signal. This misalignment can result from the lack of synchronization of the RF communication signal 530 time-base (e.g., $T_{RF}$) and the sensor time-base (e.g., $T_{sense}$). To the extent that the RF communication signals 530 couple with the sensor output signals 628A-628C, it can be understood that each sensor sample will include a different sampling of the RFI envelope 532, and these different samplings can create a modulation of the sensor output signal (e.g., the RFI envelope can be aliased into the bandwidth of interest of the sensor output signals).

In some examples, such as illustrated in FIG. 6, the sample rate (e.g., $f_{sense}$) of sensor circuitry can be slower than sub-frame (or frame) rate (e.g., $f_{RF}$) of a nearby RF communication signal (e.g., 530 above). The minimum rate at which a signal can be sampled without introducing errors (e.g., aliasing), also referred to as the Nyquist frequency ($f_N$), is twice the highest frequency present in the sampled signal. This means that for $f_{sense} < f_{RF}$ (as illustrated in FIG. 6), aliasing of the RF communication signal 530 will occur during sampling. The effect of the aliasing can be that components of the RF communication signal 530 can appear to exist at frequencies other than $f_{RF}$ and its harmonics (as explained in FIG. 5B above). In some examples, the sensor (e.g., sensor 306 above) can produce a sensor signal 738 of interest (e.g., a PPG signal) that falls in a bandwidth of interest $B_{sense}$ between a low frequency $f_L$ and a high frequency $f_H$. For one example sensor, the bandwidth of interest can be 1-10 Hz. However, it is understood that other bandwidths of interest for sensor output signals (e.g., 628A-628C) can be used while remaining within the scope of the disclosure.

Figure 7:
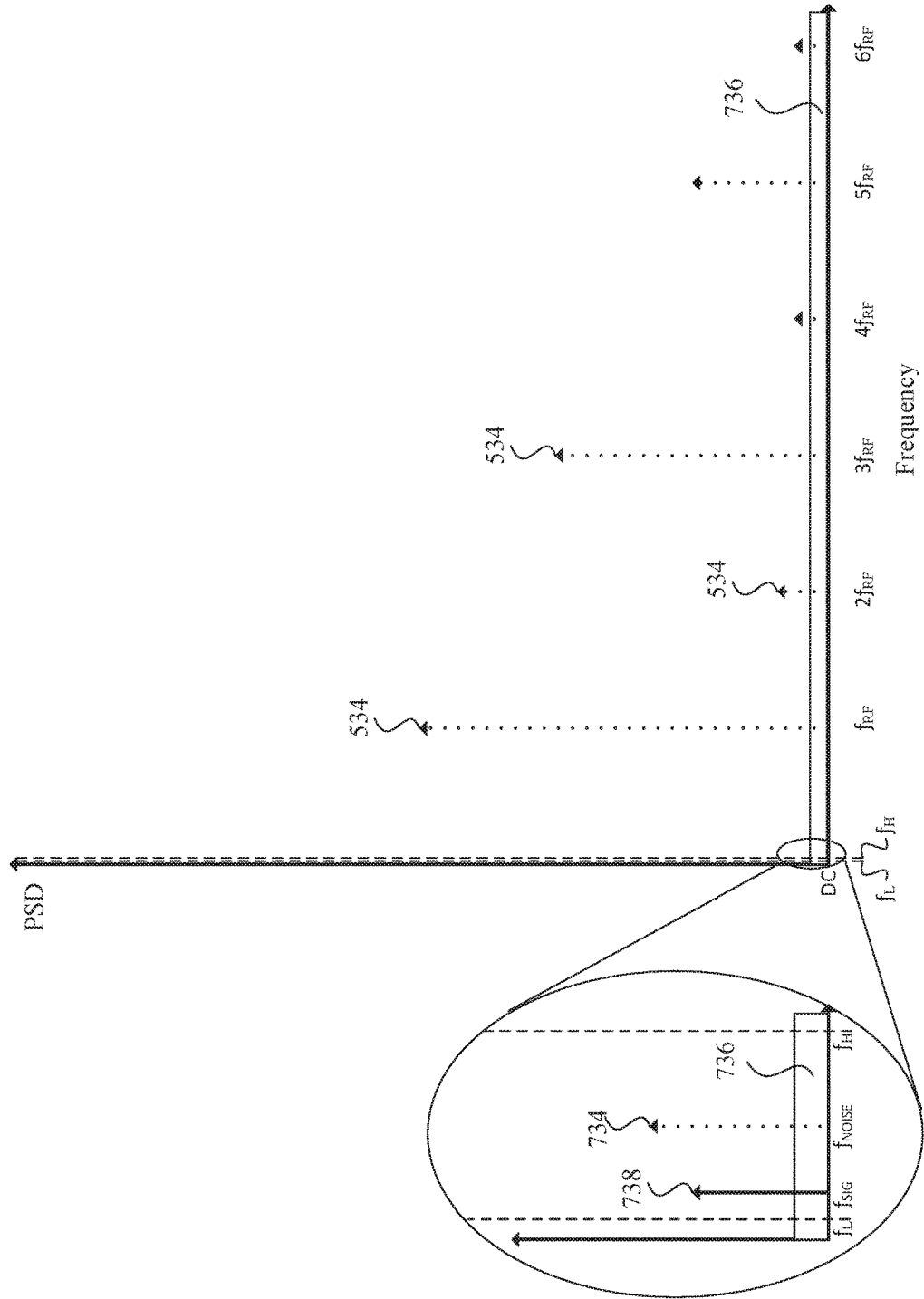
FIG. 7 illustrates a frequency domain representation of an exemplary sensor output spectrum of a sensor that is not synchronized with nearby RF circuitry according to examples of the disclosure.

FIG. 7 illustrates a frequency domain representation of an exemplary sensor output spectrum of a sensor (e.g., sensor 306 above) that is not synchronized with nearby RF circuitry (e.g., 302 above) according to examples of the disclosure. On the right hand side of FIG. 7, the frequency domain representation of RFI envelope (e.g., 532 above) frequency components 534 (e.g., as illustrated in FIG. 5B) are shown along with the bandwidth of interest $B_{sense}$ between low frequency $f_L$ (e.g., 1 Hz) and a high frequency $f_H$ (e.g., 10 Hz), represented by dashed lines. On the left side of FIG. 7, a zoomed in view of the bandwidth of interest portion of the spectrum (not to scale) is depicted. In some examples, aliased signal 734 of the RFI envelope (e.g., 532 above) frequency components 534 can fall within the bandwidth of interest at a frequency $f_{NOISE}$ (e.g., an aliased signal at 5 Hz). In some examples, the aliased signal 734 can have a greater magnitude (e.g., larger signal) than the signal of interest 738. In some examples, a sensor signal of interest (e.g., a PPG signal) can be detected in the bandwidth of interest $B_{sense}$ as a signal at frequency $f_{SIG}$ (e.g., 2 Hz). While the signal of interest 538 and the aliased signal 734 are illustrated with comparable amplitudes, in some examples the aliased signal can be much larger (e.g., an order of magnitude larger) than the signal of interest 738. In addition, white noise 736 can reduce the signal-to-noise ratio (SNR) of the sampled signal. In some examples, the aliased signal 734 and white noise 736 can make the signal of interest 738 very difficult or impossible to detect. Accordingly, techniques for removing the aliased signal 734 from the bandwidth of interest are described in further detail in the examples below.

Figure 8:
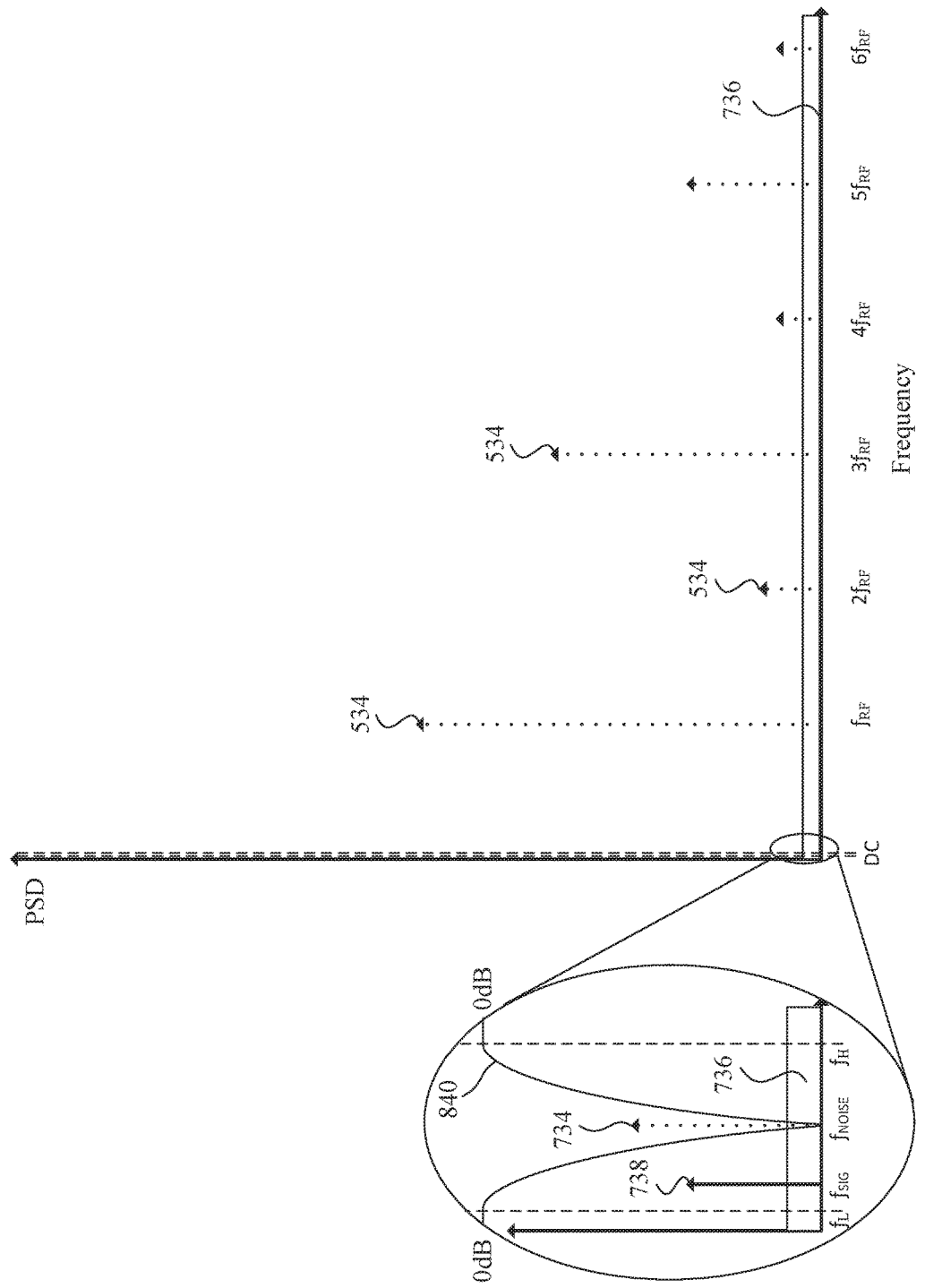
FIG. 8 illustrates an example notch filter for rejecting an aliased signal within the bandwidth of interest for a sensor signal according to examples of the disclosure.

FIG. 8 illustrates an example notch filter for rejecting an aliased signal 734 within the bandwidth of interest for a sensor signal 738 according to examples of the disclosure. In FIG. 8, the RFI envelope (e.g., 532 above) frequency components 534, signal of interest 738, aliased signal 734, and white noise 736 can all be the same as illustrated in FIG. 7. A notch filter with a frequency response 840 can be designed to reject the aliased signal 734 while only minimally attenuating the signal of interest 738. However, as illustrated, the notch filter can also attenuate the signal of interest 738, which can reduce the effective SNR of the sensor to unacceptably low levels. Furthermore, selecting an appropriate notch filter 840 assumes that the frequency $f_{NOISE}$ of the aliased signal 734 occurs at a relatively fixed frequency within the band of interest. This assumption may not necessarily be valid as the time-base of the RF communication signals 534 can be asynchronous with the time-base of the sensor circuitry (as described above), resulting in variability of the aliasing frequency $f_{NOISE}$. It should be understood that the 0 dB labels in FIG. 8 are used to illustrate that the frequency response 840 of the notch filter will attenuate signals within the bandwidth of interest, but the 0 dB labels are not meant to be indicative of the signal strength of the signal of interest 738, the aliased signal 734, or the white noise 736. Alternative techniques for removing the RF interference are discussed in further detail below.

Figure 9:
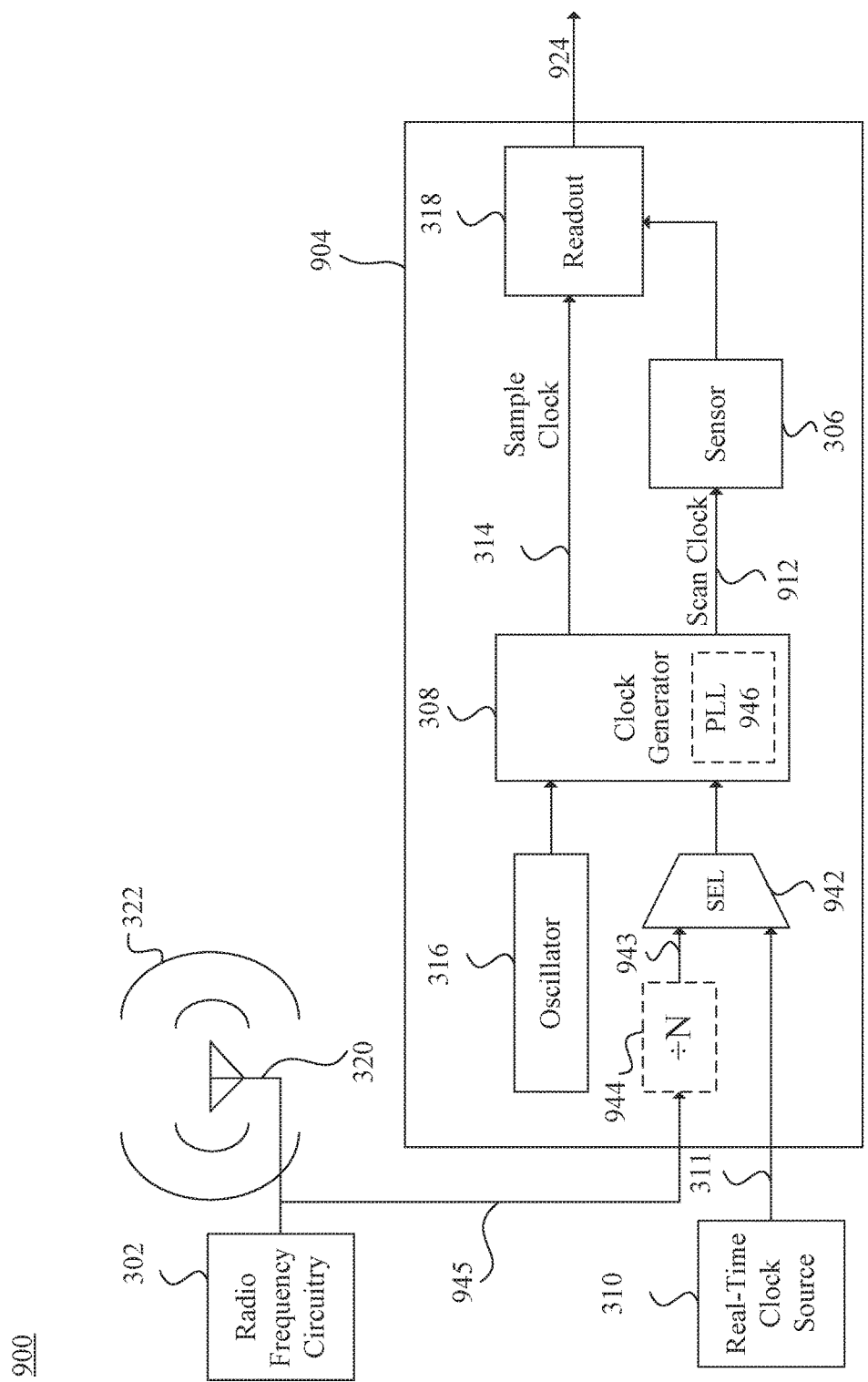
FIG. 9 illustrates an alternative exemplary block diagram of device utilizing clock synchronization between radio frequency circuitry and precision sensor circuitry according to examples of the disclosure.

FIG. 9 illustrates an exemplary block diagram of a device 900 (which can correspond to device 300 above) utilizing clock synchronization between radio frequency circuitry 302 and precision sensor circuitry 904 (which can correspond to precision sensor circuitry 304) according to examples of the disclosure. FIG. 9 illustrates a block diagram for addressing the radio frequency interferences described in FIGS. 3-8 above. In some examples, precision sensor circuitry 904 can include oscillator 316, clock generator 308, and readout circuitry 318 as described in FIG. 3 above. In some examples clock generator 308 can produce sample clock 314 that can be utilized as a clock for readout circuitry 318, for example providing a clock for an analog-to-digital converter for converting analog sensor 306 output signals into digital signals 924 for further processing (e.g., for analyzing detected PPG signals to determine a user's heart rate). In some examples, antenna 320 can be coupled to RF circuitry 302 and configured to transmit and/or receive RF communication signals 322. In some examples, the clock generator 308 can include one or more divide by N clock generators for generating clocks of different desired output clock frequencies based on reference input clock sources. In addition to providing a RTC source 310 as a clock input to the clock generator 308 for generating scan clock 912, a clock selection circuit (SEL) 942 (e.g., a multiplexer) can be included for allowing selection of an alternative clock source to the clock generator. The clock selection circuit 942 can be used to select between RTC source 310 and a second input 943 from a second clock source (e.g., a frame clock or a sub-frame clock, or a clock derived from the frame clock or sub-frame clock). The second input 943 of the clock selection circuit 942 can be connected to a variable clock divider 944 that can receive its input from the RF circuitry 302. In some examples, the variable clock divider 944 can be included within the clock generator 308. In some examples, the variable clock divider 944 can receive an RF frame timing signal 945 (e.g., a frame clock or a sub-frame clock) used to generate and/or based on the RF frame timing of the RF circuitry 302 transmissions described above (e.g., a 1 kHz clock pulse corresponding to the 1 ms sub-frame period or a 100 Hz clock pulse corresponding to the 10 ms frame period). In some examples, an optional variable clock divider 944 can be used to scale the RF frame timing signal 945 to closely match the scan clock 912 frequency generated from the RTC source 310. As one example, for a scan clock 912 rate of 256 Hz based on the RTC source 310 (e.g., 32.768 kHz RTC clock divided by 128) can be most closely matched by a scan clock rate of 250 Hz based on the RF frame timing signal 945 (e.g., 1 kHz clock divided by 4). In some examples, the RF frame timing signal 945 can have a frequency lower than the desired scan clock 912 frequency (e.g., an RF frame timing signal at 100 Hz and a desired scan clock frequency of 250 Hz). In some examples, a phase locked loop (PLL) 946 can be added to clock generator 308 or can replace and/or perform the role of the optional variable clock divider 944 for generating the scan clock 912. By using the RF frame timing signal 945 to generate the scan clock 912, RF communication signal 322 aliasing can be moved out of the bandwidth of interest $B_{sense}$, alleviating the impact of the RFI on sensor 306 operation (e.g., improving the SNR of sensor 306 sampled output). However, when RF circuitry 302 is inactive, the RF frame timing signal 945 may no longer be provided, while data from sensor 306 may still be desired. In some examples, the clock selection circuit 942 can switch the clock source to the RTC source 310 when the RF frame timing signal 945 is inactive. In some examples, the RFI from RF communication signals 322 can also cease when the RF frame timing signal 945 is inactive, which can result in no RFI being present that can be aliased into the bandwidth of interest $B_{sense}$ during this time period. As a result, the RTC source 310 can be used to generate the scan clock 912 when the RF communication signals 322 are inactive without concern for aliasing of the RFI into the bandwidth of interest $B_{sense}$. In some examples, a flag signal (not shown) indicative of RF communication activity can be provided directly from the RF circuitry 302 to toggle the selected clock source. In some examples, the clock selection circuitry 942 can intelligently determine whether the RF frame timing signal 945 is active and stable, and based on the determination select between the RF frame timing signal and the RTC source 310 automatically.

Figure 10:
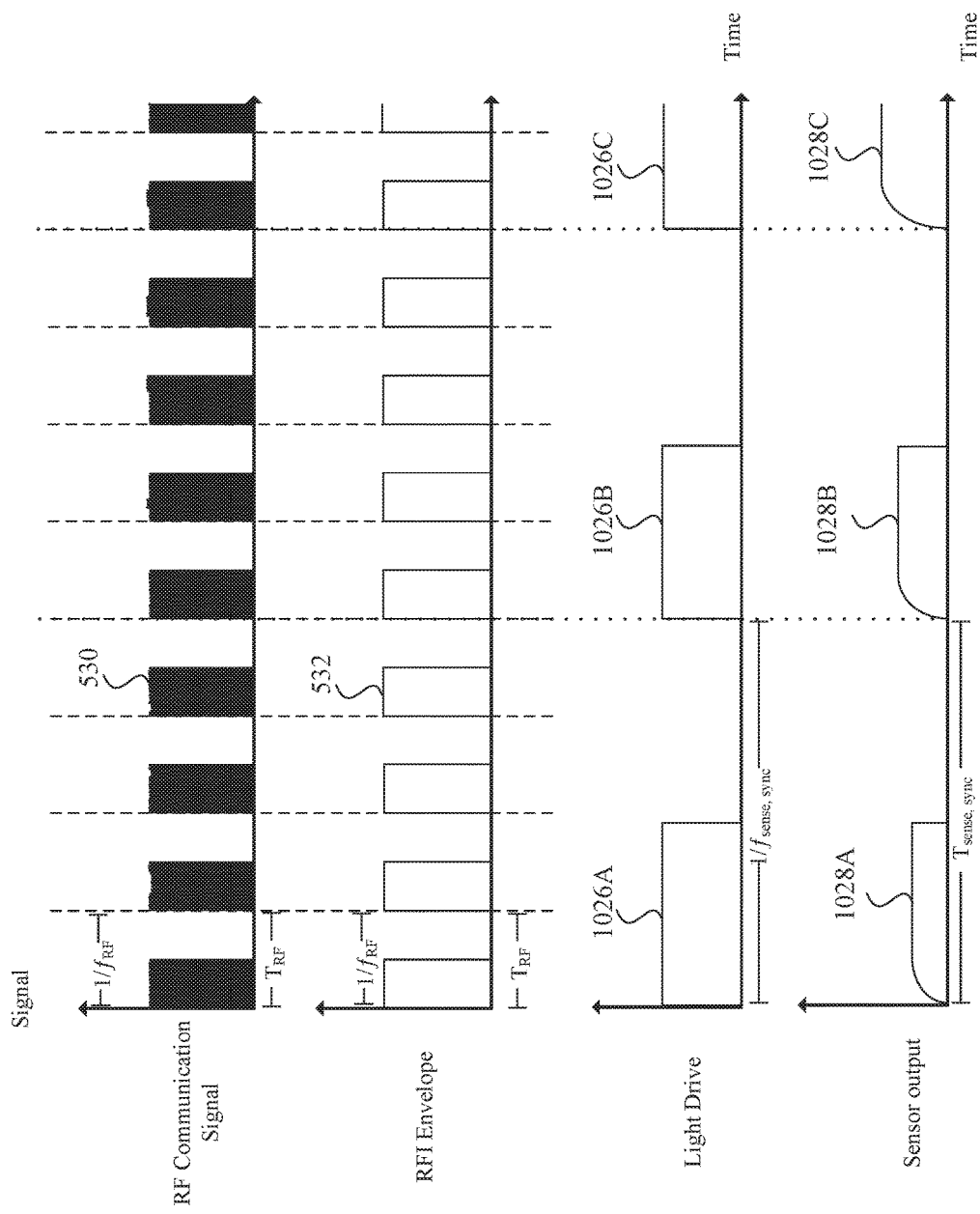
FIG. 10 illustrates synchronized timing signals of RF communication signals and sensor signals according to examples of the disclosure.

In an alternative example, the RF frame timing signal 945 may not be available for use as a clock source even when the RF communication signals 322 are active. In such examples, the RTC source 310 can be used as a clock source for an optional PLL 946 that can be included in clock generator 308 or be provided as a separate component. The PLL 946 output signal based on the RTC source 310 can be used to generate a scan clock 912 that is a multiple of the RF frame timing (e.g., a frame clock or a sub-frame clock) for providing synchronized timing between the RF circuitry and the sensor circuitry. In the present example, RF communication signal 322 aliasing can be moved out of the bandwidth of interest $B_{sense}$, alleviating the impact of the RFI on sensor 306 operation (e.g., improving the SNR of sensor 306 sampled output) even without generating the scan clock 912 directly from the RF frame timing signal 945. In some examples, the scan clock 912 of the present example can be utilized only when the RF communication signals 322 are active. In some examples, the scan clock 912 of the present example can be utilized both when the RF communication signals 322 are active and when the RF communication signals are inactive. While the discussion above applies to the specific architecture illustrated in FIG. 9, it should be understood that the same principles can be applied to any sensing architecture that can be configured to sense signals within a particular frequency band (e.g., $B_{sense}$). Furthermore, it should be understood that the noise removal techniques described above can be applied generally to noise sources that can couple to a sensor within a bandwidth of interest (e.g., $B_{sense}$) and are not limited to a particular noise source such as an on-chip RF communication signal 322. FIG. 10 below illustrates synchronized timing signals of the RF communication signal 322 and sensor 306 signals.

FIG. 10 illustrates synchronized timing signals of RF communication signals (e.g., 322 above) and sensor (e.g., 306 above) signals according to examples of the disclosure. FIG. 10 includes the RF communication signals 530 and RFI envelope 532 as described above regarding FIG. 5 having a sub-frame period $T_{RF}$ (e.g., 1 ms in the case of LTE). In some examples, the sensor (e.g. sensor 306 above) scan period $T_{sense,\ sync}$ can be synchronized with $T_{RF}$. In other words, the sensor scan period $T_{sense,\ sync}$ can be an integer multiple of the sub-frame period $T_{RF}$ (e.g., $T_{sense,\ sync}$ illustrated as $4*T_{RF}$). In some examples, the synchronized operations can mean that stimulation signals 1026A, 1026B, and 1026C become active at the beginning of a sub-frame, and the sensor output signals 1028A, 1028B, and 1028C can also be sampled with a fixed alignment relative to the RF communication signals 530 and RFI envelope 532. Thus, in some examples, synchronizing sensor (e.g., sensor 306 above) operations can be achieved by generating a scan clock (e.g., with clock generator 308 above) directly from the RF communication signal 530 clock domain. FIG. 10 illustrates that the clock synchronization technique described above can also be referred to as scan rate locking as the sensor scans and RF communication sub-frames can be locked relative to one another as a result of the clock synchronization. Results of the scan rate locking in the frequency domain will be described and illustrated in more detail below. It should be understood from the above that sub-frames, frames and signals that can be derived from frames and/or sub-frames can be utilized to synchronize sensor scan periods (e.g., $T_{sense,\ sync}$) with RF communication signals 530.

Figure 11:
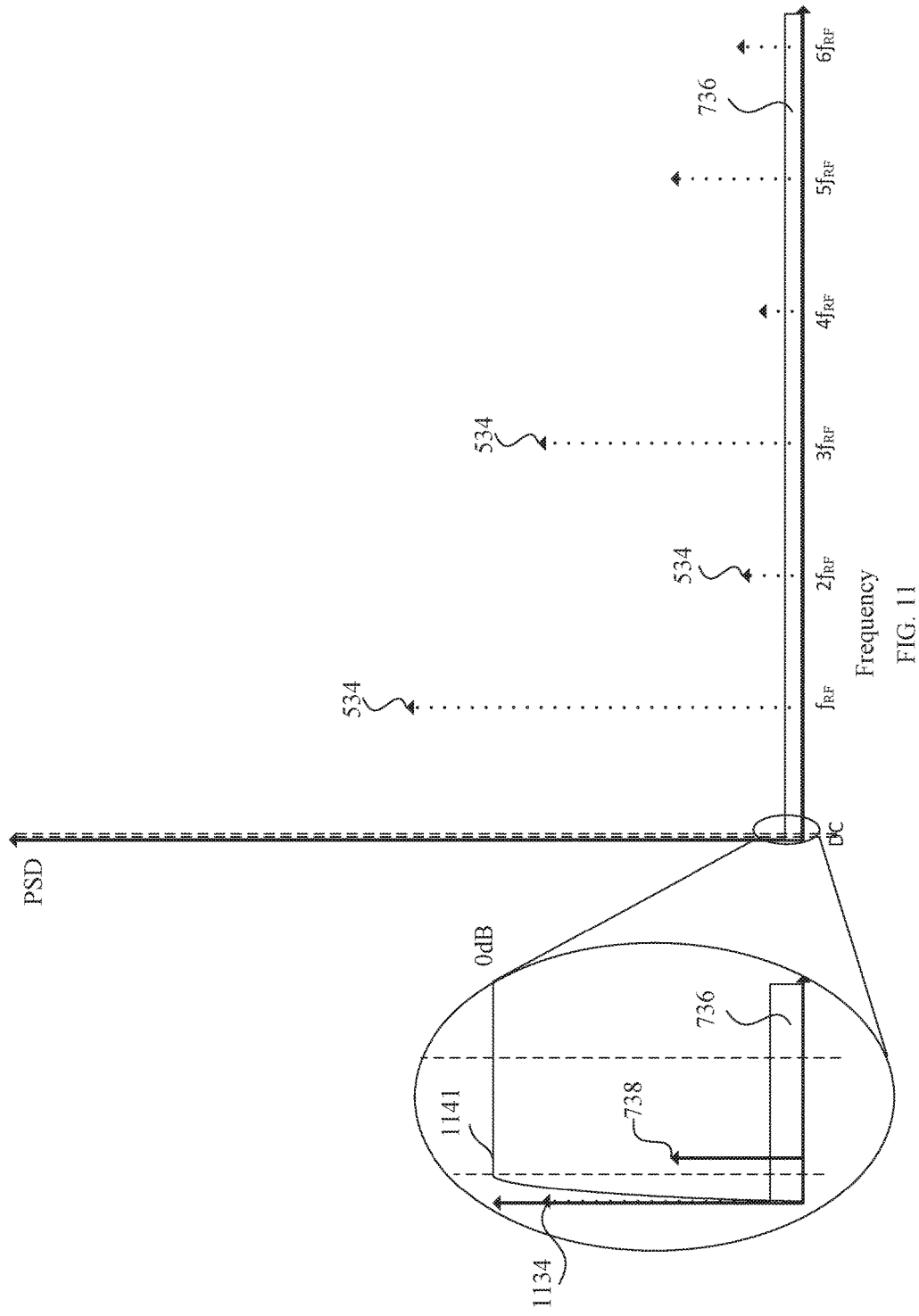
FIG. 11 illustrates a frequency domain representation of an exemplary output spectrum of a sensor that is synchronized with nearby RF circuitry according to examples of the disclosure.

FIG. 11 illustrates a frequency domain representation of an exemplary output spectrum of a sensor (e.g., sensor 306 above) that is synchronized with nearby RF circuitry (e.g., 302 above) according to examples of the disclosure. In the illustration, the frequency components resulting from RFI envelope 532 are represented the same as above in FIGS. 5, 7, and 8. In some examples, where the RF envelope fundamental frequency $f_{RF}$ and its harmonics, $2f_{RF}$, $3f_{RF}$, etc. all occur at integer multiples of sensor scan rate $f_{sense,\ sync}$, (i.e., when the clocks are synchronized) an aliased signal 1134 of the RFI envelope (e.g., 532 above) frequency components 534 can occur at DC, rather than falling within the bandwidth of interest $B_{sense}$ between low frequency $f_L$ (e.g., 1 Hz) and high frequency $f_H$ (e.g., 10 Hz). A high pass filter having a frequency response 1141 can be used to remove the DC aliased component 1134 without attenuating the signal of interest 738. It should be understood that the 0 dB label in FIG. 11 is used to illustrate that the frequency response 1141 of the high pass filter will not attenuate signals within the bandwidth of interest, but is not indicative of the signal strength of the signal of interest 738 or the aliased signal 1134. In some examples, the SNR of signal of interest 738 will continue to be affected by white noise 736, but the effects on SNR of aliased signal 1134 resulting from the RF envelope frequency components 534 can be significantly improved. Thus, FIG. 11 illustrates how scan rate locking can be used to remove RF interferences according to examples of the disclosure.

It can be further understood from the FIG. 11 that in some examples, a DC component of the sensor output can be larger for a sensor that is synchronized with RF communication signals (e.g., a sensor scan period synchronized with the RF communication signals, such as the RF frame timing, the RF sub-frame timing, etc.) than a sensor that is not synchronized with the RF communication signals. Thus, in some examples, for a fixed signal strength of RF communication signals, a DC component of the sensor output when the sensor is scanned at a synchronous rate can be larger than a DC component of the sensor output when the sensor is scanned at an asynchronous rate.

Figure 12:
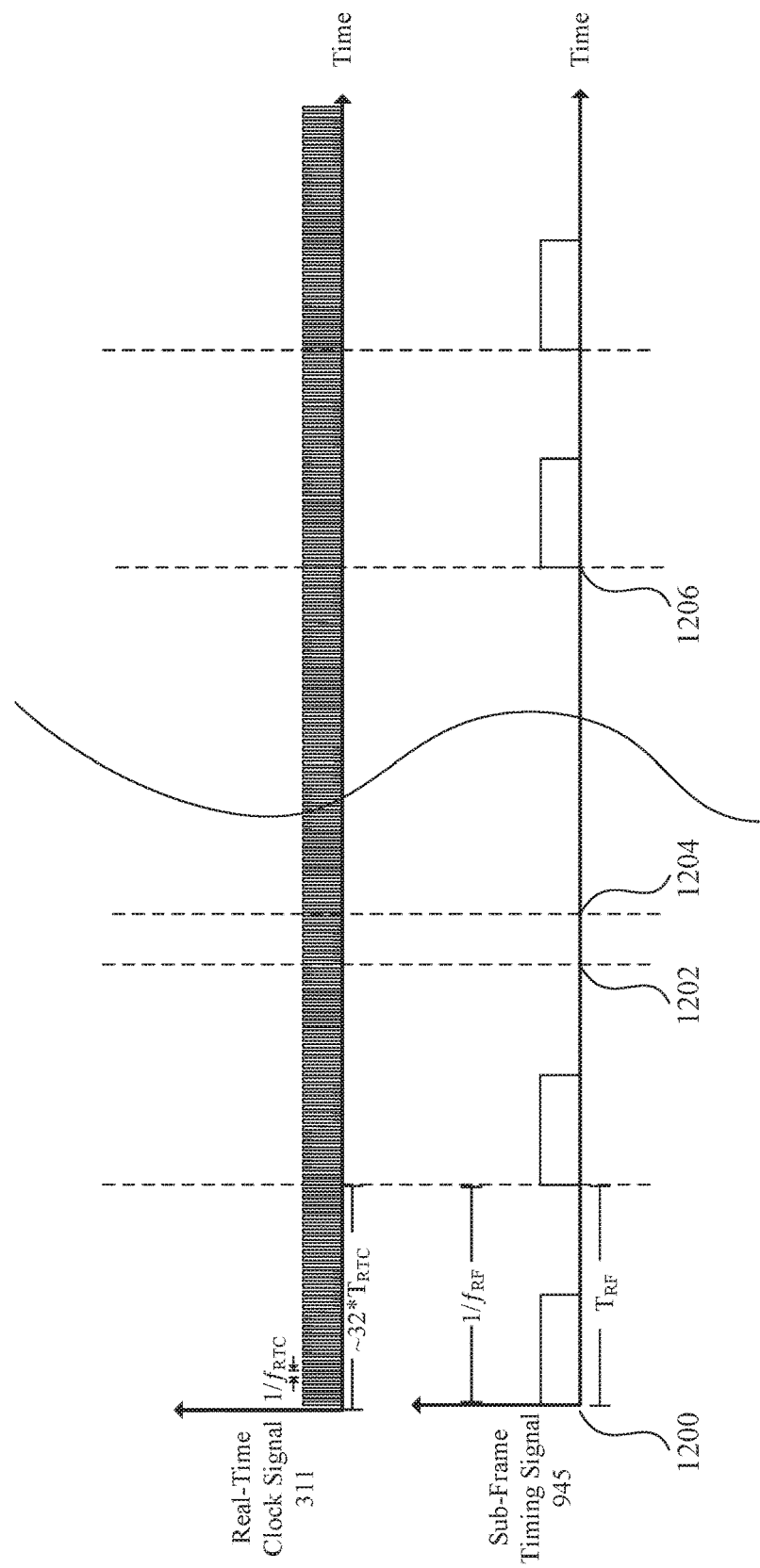
FIG. 12 illustrates an exemplary timing diagram of a RTC clock signal and an RF frame timing signal according to examples of the disclosure.

FIG. 12 illustrates an exemplary timing diagram of a RTC clock signal 311 (e.g., from RTC source 310 in FIG. 3 above) and a RF frame timing signal (e.g., 945 above) according to examples of the disclosure. The following description of FIG. 12 refers to elements and signals illustrated in FIG. 9 above. In some examples, the RTC clock signal 311 can operate at a frequency of 32.768 kHz, while the RF frame timing signal 945 can have a 1 kHz frequency (e.g., for LTE). In some examples, during an active period 1200 of the RF frame timing signal 945, the clock selection circuit 942 can use the RF frame timing signal 945 for generating the scan clock 912 for sensor 306. In some examples, if the next RF frame timing signal 945 rising edge does not occur (e.g., at time 1202), the clock selection circuit can switch to the RTC clock signal 311 for generating the scan clock 912. In some examples, the clock selection circuit 942 can wait for a threshold number of RTC clock signal 311 counts (e.g., 8 clock cycles of the RTC clock) prior to switching clock sources. In some examples, once the threshold number of RTC clock pulses is reached 1204, the clock source can be switched. In some examples, instead of counting pulses, the RF circuitry 302 can provide a flag to the clock selection circuit 942 that can immediately indicate an end of RF communication, and the clock selection circuit can switch to the RTC clock at time 1202 (or very shortly thereafter). In some examples, when the RF frame timing signal 945 resumes at time 1206, the clock selection circuit 942 can also control switching the clock source from the RTC clock signal 311 to the RF frame timing signal. The clock selection circuit 942 can either directly detect the presence of the RF frame timing signal 945, or the clock selection circuit can receive a flag provided by the RF circuitry 302 used to indicate the beginning of RF communication. In some examples, the clock selection circuit 942 can wait for several clock cycles of the RF frame timing signal 945 to pass to ensure a stable clock source exists for generating the scan clock 912 prior to switching away from the RTC clock signal.

Figure 13:
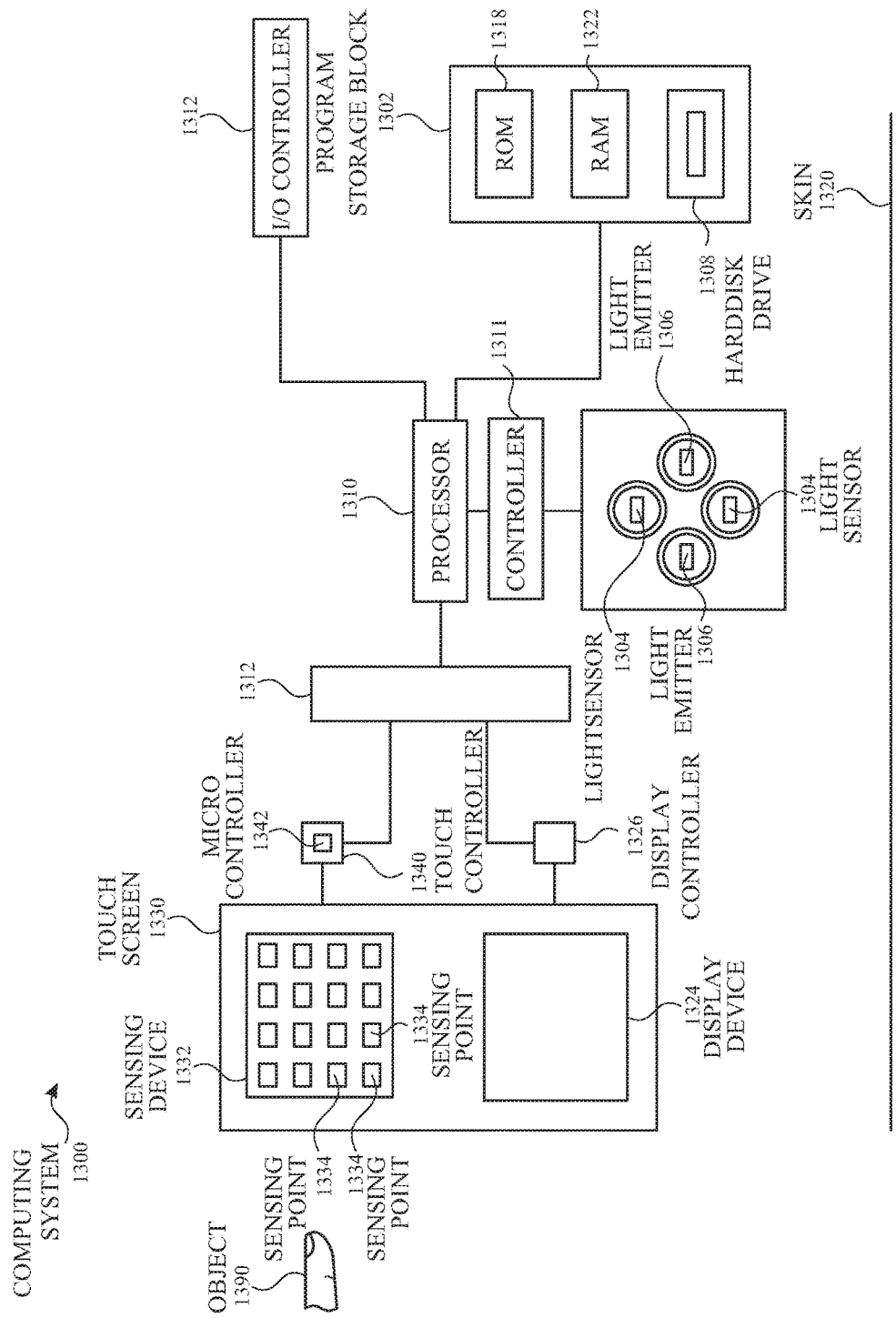
FIG. 13 illustrates an exemplary block diagram of a computing system comprising light emitters and light sensors for measuring a signal associated with a user's physiological state according to examples of the disclosure.

FIG. 13 illustrates an exemplary block diagram of a computing system comprising light emitters and light sensors for measuring a signal associated with a user's physiological state according to examples of the disclosure. Computing system 1300 can correspond to any of the computing devices illustrated in FIGS. 1A-1C. Computing system 1300 can include a processor 1310 configured to execute instructions and to carry out operations associated with computing system 1300. For example, using instructions retrieved from memory, processor 1310 can control the reception and manipulation of input and output data between components of computing system 1300. Processor 1310 can be a single-chip processor or can be implemented with multiple components.

In some examples, processor 1310 together with an operating system can operate to execute computer code and produce and use data. The computer code and data can reside within a program storage block 1302 that can be operatively coupled to processor 1310. Program storage block 1302 can generally provide a place to hold data that is being used by computing system 1300. Program storage block 1302 can be any non-transitory computer-readable storage medium, and can store, for example, history and/or pattern data relating to PPG signal and perfusion index values measured by one or more light sensors such as light sensors 1304. By way of example, program storage block 1302 can include Read-Only Memory (ROM) 1318, Random-Access Memory (RAM) 1322, hard disk drive 1308 and/or the like. The computer code and data could also reside on a removable storage medium and loaded or installed onto the computing system 1300 when needed. Removable storage mediums include, for example, CD-ROM, DVD-ROM, Universal Serial Bus (USB), Secure Digital (SD), Compact Flash (CF), Memory Stick, Multi-Media Card (MMC) and a network component.

Computing system 1300 can also include an input/output (I/O) controller 1312 that can be operatively coupled to processor 1310, or it can be a separate component as shown. I/O controller 1312 can be configured to control interactions with one or more I/O devices. I/O controller 1312 can operate by exchanging data between processor 1310 and the I/O devices that desire to communicate with processor 1310. The I/O devices and I/O controller 1312 can communicate through a data link. The data link can be a one-way link or a two-way link. In some cases, I/O devices can be connected to I/O controller 1312 through wireless connections. By way of example, a data link can correspond to PS/2, USB, Firewire, IR, RF, Bluetooth or the like.

Computing system 1300 can include a display device 1324 that can be operatively coupled to processor 1310. Display device 1324 can be a separate component (peripheral device) or can be integrated with processor 1310 and program storage block 1302 to form a desktop computer (e.g., all-in-one machine), a laptop, handheld or tablet computing device of the like. Display device 1324 can be configured to display a graphical user interface (GUI) including perhaps a pointer or cursor as well as other information to the user. By way of example, display device 1324 can be any type of display including a liquid crystal display (LCD), an electroluminescent display (ELD), a field emission display (FED), a light emitting diode display (LED), an organic light emitting diode display (OLED) or the like.

Display device 1324 can be coupled to display controller 1326 that can be coupled to processor 1310. Processor 1310 can send raw data to display controller 1326, and display controller 1326 can send signals to display device 1324. Data can include voltage levels for a plurality of pixels in display device 1324 to project an image. In some examples, processor 1310 can be configured to process the raw data.

Computing system 1300 can also include a touch screen 1330 that can be operatively coupled to processor 1310. Touch screen 1330 can be a combination of sensing device 1332 and display device 1324, where the sensing device 1332 can be a transparent panel that is positioned in front of display device 1324 or integrated with display device 1324. In some cases, touch screen 1330 can recognize touches and the position and magnitude of touches on its surface. Touch screen 1330 can report the touches to processor 1310, and processor 1310 can interpret the touches in accordance with its programming. For example, processor 1310 can perform tap and event gesture parsing and can initiate a wake of the device or powering on one or more components in accordance with a particular touch.

Touch screen 1330 can be coupled to a touch controller 1340 that can acquire data from touch screen 1330 and can supply the acquired data to processor 1310. In some cases, touch controller 1340 can be configured to send raw data to processor 1310, and processor 1310 can process the raw data. For example, processor 1310 can receive data from touch controller 1340 and can determine how to interpret the data. The data can include the coordinates of a touch as well as pressure exerted. In some examples, touch controller 1340 can be configured to process raw data itself. That is, touch controller 1340 can read signals from sensing points 1334 located on sensing device 1332 and can turn the signals into data that the processor 1310 can understand.

Touch controller 1340 can include one or more microcontrollers such as microcontroller 1342, each of which can monitor one or more sensing points 1334. Microcontroller 1342 can, for example, correspond to an application specific integrated circuit (ASIC), which works with firmware to monitor the signals from sensing device 1332, process the monitored signals, and report this information to processor 1310.

One or both of display controller 1326 and touch controller 1340 can perform filtering and/or conversion processes. Filtering processes can be implemented to reduce a busy data stream to prevent processor 1310 from being overloaded with redundant or non-essential data. The conversion processes can be implemented to adjust the raw data before sending or reporting them to processor 1310.

In some examples, sensing device 1332 can be based on capacitance. When two electrically conductive members come close to one another without actually touching, their electric fields can interact to form a capacitance. The first electrically conductive member can be one or more of the sensing points 1334, and the second electrically conductive member can be an object 1390 such as a finger. As object 1390 approaches the surface of touch screen 1330, a capacitance can form between object 1390 and one or more sensing points 1334 in close proximity to object 1390. By detecting changes in capacitance at each of the sensing points 1334 and noting the position of sensing points 1334, touch controller 1340 can recognize multiple objects, and determine the location, pressure, direction, speed and acceleration of object 1390 as it moves across the touch screen 1330. For example, touch controller 1340 can determine whether the sensed touch is a finger, tap, or an object covering the surface.

Sensing device 1332 can be based on self-capacitance or mutual capacitance. In self-capacitance, each of the sensing points 1334 can be provided by an individually charged electrode. As object 1390 approaches the surface of the touch screen 1330, the object can capacitively couple to those electrodes in close proximity to object 1390, thereby stealing charge away from the electrodes. The amount of charge in each of the electrodes can be measured by the touch controller 1340 to determine the position of one or more objects when they touch or hover over the touch screen 1330. In mutual capacitance, sensing device 1332 can include a two layer grid of spatially separated lines or wires (not shown), although other configurations are possible. The upper layer can include lines in rows, while the lower layer can include lines in columns (e.g., orthogonal). Sensing points 1334 can be provided at the intersections of the rows and columns. During operation, the rows can be charged, and the charge can capacitively couple from the rows to the columns. As object 1390 approaches the surface of the touch screen 1330, object 1390 can capacitively couple to the rows in close proximity to object 1390, thereby reducing the charge coupling between the rows and columns. The amount of charge in each of the columns can be measured by touch controller 1340 to determine the position of multiple objects when they touch the touch screen 1330.

Computing system 1300 can also include one or more light emitters such as light emitters 1306 and one or more light sensors such as light sensors 1304 proximate to skin 1320 of a user. Light emitters 1306 can be configured to generate light, and light sensors 1304 can be configured to measure a light reflected or absorbed by skin 1320, vasculature, and/or blood of the user. Light sensor 1304 can send measured raw data to processor 1310, and processor 1310 can perform noise and/or artifact cancellation to determine the PPG signal and/or perfusion index. Processor 1310 can dynamically activate light emitters and/or light sensors and dynamically reconfigure the aperture properties based on an application, user skin type, and usage conditions. In some examples, controller 1311 (which can correspond to precision sensor circuitry 304 above), can include timing generation (which can correspond to clock generator 308 above) for light emitters 1306 and light sensors 1304, as well as readout circuitry (which can correspond to readout circuitry 318 above) for sampling, converting, and filtering output signals from the light sensors 1304 and reporting the outputs to the processor 1310. In some examples, some light emitters and/or light sensors can be activated, while other light emitters and/or light sensors can be deactivated to conserve power, for example. In some examples, processor 1310 can store the raw data and/or processed information in a ROM 1318 or RAM 1322 for historical tracking or for future diagnostic purposes.

Figure 14:
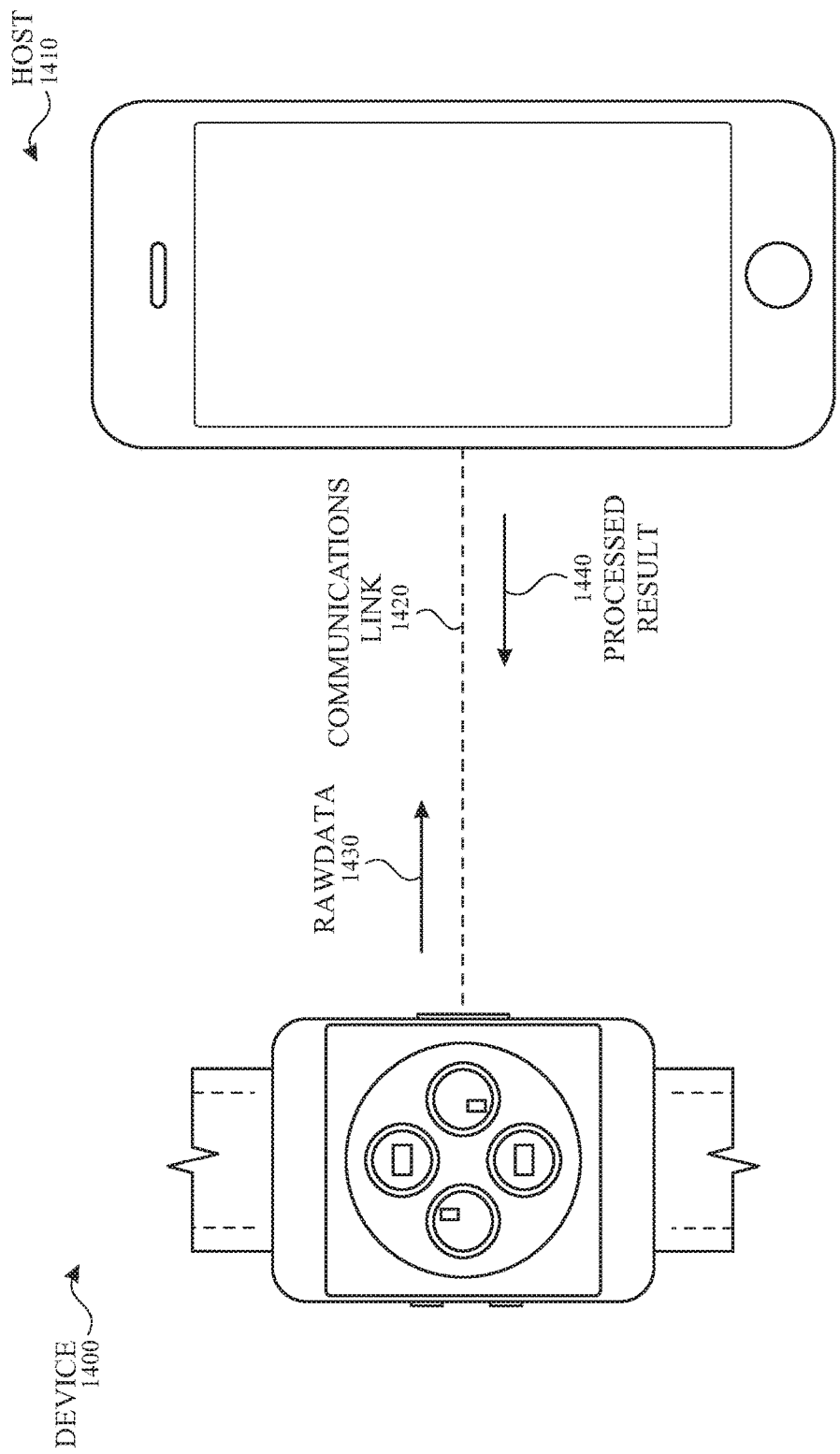
FIG. 14 illustrates an exemplary configuration in which an electronic device is connected to a host according to examples of the disclosure.

In some examples, the light sensors can measure light information and a processor can determine a PPG signal and/or perfusion index from the reflected or absorbed light. Processing of the light information can be performed on the device as well. In some examples, processing of light information need not be performed on the device itself. FIG. 14 illustrates an exemplary configuration in which an electronic device is connected to a host according to examples of the disclosure. Host 1410 can be any device external to device 1400 including, but not limited to, any of the systems illustrated in FIGS. 1A-1C or a server. Device 1400 can be connected to host 1410 through communications link 1420. Communications link 1420 can be any connection including, but not limited to, a wireless connection and a wired connection. Exemplary wireless connections include Wi-Fi, Bluetooth, Wireless Direct and Infrared. Exemplary wired connections include Universal Serial Bus (USB), FireWire, Thunderbolt, or any connection requiring a physical cable.

In operation, instead of processing light information from the light sensors on the device 1400 itself, device 1400 can send raw data 1430 measured from the light sensors over communications link 1420 to host 1410. Host 1410 can receive raw data 1430, and host 1410 can process the light information. Processing the light information can include canceling or reducing any noise due to artifacts and determining physiological signals such as a user's heart rate. Host 1410 can include algorithms or calibration procedures to account for differences in a user's characteristics affecting PPG signal and perfusion index. Additionally, host 1410 can include storage or memory for tracking a PPG signal and perfusion index history for diagnostic purposes. Host 1410 can send the processed result 1440 or related information back to device 1400. Based on the processed result 1440, device 1400 can notify the user or adjust its operation accordingly. By offloading the processing and/or storage of the light information, device 1400 can conserve space and power-enabling device 1400 to remain small and portable, as space that could otherwise be required for processing logic can be freed up on the device.

The firmware can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer-readable storage medium" can be any medium (excluding signals) that can contain or store the program for use by or in connection with the instruction execution system, apparatus, or device. The computer-readable storage medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The firmware can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

Therefore, according to the above, some examples of the disclosure are directed to a method comprising generating a sensor scan rate synchronized with radio frequency communication signals transmitted proximate to a sensor and while the radio frequency communication signals are being transmitted, sensing data at the sensor proximate to the radio frequency communications signals at the sensor scan rate. Additionally or alternatively to one or more of the examples disclosed above, in some examples, the method further comprises generating a second sensor scan rate based on a reference clock source, the second sensor scan rate being asynchronous to the radio frequency communication signals and during a second time interval, sensing data at the sensor proximate to the radio frequency communication signals at the second sensor scan rate. Additionally or alternatively to one or more of the examples disclosed above, in some examples, the method further comprises determining whether the radio frequency communication signals are active, sensing sensor data at the sensor scan rate in accordance with a determination that the radio frequency communication signals are active and sensing sensor data at the second sensor scan rate in accordance with a determination that the radio frequency communication signals are inactive. Additionally or alternatively to one or more of the examples disclosed above, in some examples, determining whether the radio frequency communication signals are active comprises receiving a flag signal from a radio frequency circuitry located proximate to the sensor. Additionally or alternatively to one or more of the examples disclosed above, in some examples, determining whether the radio frequency communication signals are active comprises detecting a presence of communication frames in the radio frequency signals, the communication frames having an associated communication frame rate. Additionally or alternatively to one or more of the examples disclosed above, in some examples, an output of the sensor at the second scan rate while the radio frequency communication signals are active results includes a first DC value based on the radio frequency signals an output of the sensor at the scan rate while the radio frequency communication signals are active includes a second DC value based on the radio frequency signals, the second value greater than the first value and a difference between the first DC value and the second DC value exists for a fixed signal strength of the radio frequency communication signals. Additionally or alternatively to one or more of the examples disclosed above, in some examples, the sensor scan rate is an integer multiple or integer sub-multiple of a communication frame rate of the radio frequency communication signals. Additionally or alternatively to one or more of the examples disclosed above, in some examples, generating the sensor scan rate synchronized with a radio frequency communication signals comprises receiving a frame timing signal or sub-frame timing signal from radio frequency circuitry and scaling the received frame timing signal or sub-frame timing signal to a desired sensor scan rate frequency.

Some examples of the disclosure are directed to a non-transitory computer readable storage medium having stored thereon a set of instructions, that when executed by a processor causes the processor to generate a sensor scan rate synchronized with radio frequency communication signals transmitted proximate to a sensor and while the radio frequency signals are being transmitted, sense data at the sensor proximate to the radio frequency communications signals at the sensor scan rate. Additionally or alternatively to one or more of the examples disclosed above, in some examples, the instructions further cause the processor to generate a second sensor scan rate based on a reference clock source, the second sensor scan rate being asynchronous to the communication frame rate and during a second time interval, sense data at the sensor proximate to the radio frequency communications signals at the second sensor scan rate. Additionally or alternatively to one or more of the examples disclosed above, in some examples, the instructions further cause the processor to determine whether the radio frequency circuitry is operating, sense sensor data at the sensor scan rate in accordance with a determination that a radio frequency circuitry transmitting the radio frequency communications signals is operating and sense sensor data at the second sensor scan rate in accordance with a determination that the radio frequency circuitry is not operating. Additionally or alternatively to one or more of the examples disclosed above, in some examples, determining whether the radio frequency communication signals are active comprises receiving a flag signal from the radio frequency circuitry located proximate to the sensor. Additionally or alternatively to one or more of the examples disclosed above, in some examples, determining whether the radio frequency communication signals are active comprises detecting a presence of communication frames in the radio frequency signals, the communication frames having an associated communication frame rate. Additionally or alternatively to one or more of the examples disclosed above, in some examples, an output of the sensor at the second scan rate while the radio frequency communication signals are active results includes a first DC value based on the radio frequency signals, an output of the sensor at the scan rate while the radio frequency communication signals are active includes a second DC value based on the radio frequency signals, the second value greater than the first value, and a difference between the first DC value and the second DC value exists for a fixed signal strength of the radio frequency communication signals. Additionally or alternatively to one or more of the examples disclosed above, in some examples, the sensor scan rate is an integer multiple or integer sub-multiple of a communication frame rate of the radio frequency communication signals. Additionally or alternatively to one or more of the examples disclosed above, in some examples, generating the sensor scan rate synchronized with the radio frequency communication signals comprises receiving a frame timing signal or sub-frame timing signal from radio frequency circuitry and scaling the received frame timing signal or sub-frame timing signal to a desired sensor scan rate frequency.

Some examples of the disclosure are directed to an electronic device comprising sensor circuitry configured to sense data at a scan rate, a reference clock signal generator configured to generate a reference clock signal, clock generation circuitry configured to generate the scan rate based on an input clock signal, and clock selection circuitry configured to selectively couple the input clock signal to one of the reference clock signal and a frame rate reference signal, the frame rate reference signal synchronized with radio frequency communication signals transmitted proximate to the sensor circuitry. Additionally or alternatively to one or more of the examples disclosed above, in some examples, the electronic device further comprises a light emitter, wherein the sensor circuitry is configured to sense light transmitted by the light emitter and reflected by a user's skin. Additionally or alternatively to one or more of the examples disclosed above, in some examples, the reference clock signal is asynchronous to a transmission frame rate of the radio frequency communication signals transmitted proximate to the sensor circuitry. Additionally or alternatively to one or more of the examples disclosed above, in some examples, the electronic device further comprises second clock generation circuitry configured to generate the frame rate reference signal based on a frame rate or sub-frame rate of the radio frequency communication signals. Additionally or alternatively to one or more of the examples disclosed above, in some examples, the clock selection circuitry is configured to determine whether the radio frequency communication signals are active couple the input clock signal to the frame rate reference signal in accordance with a determination that the radio frequency communication signals are active; and couple the input clock signal to the reference clock signal in accordance with a determination that the radio frequency communication signals are inactive. Additionally or alternatively to one or more of the examples disclosed above, in some examples, determining whether the radio frequency communication signals are active comprises detecting a presence of communication frames in the radio frequency communication signals, the communication frames having an associated communication frame rate. Additionally or alternatively to one or more of the examples disclosed above, in some examples, the sensor scan rate is an integer multiple or integer sub-multiple of a communication frame rate of the radio frequency communication signals when the clock selection circuitry couples the input clock signal to the frame rate reference signal.

Although examples of this disclosure have been fully described with reference to the accompanying drawings, it is to be noted that various changes and modifications will become apparent to those skilled in the art. Such changes and modifications are to be understood as being included within the scope of examples of this disclosure as defined by the appended claims.

What is claimed is:
1. A method comprising:
   generating a sensor scan rate synchronized with radio frequency communication signals transmitted proximate to a sensor;
   while the radio frequency communication signals are being transmitted, sensing data at the sensor proximate to the radio frequency communications signals at the sensor scan rate;

generating a second sensor scan rate based on a reference clock source, the second sensor scan rate being asynchronous to the radio frequency communication signals; and during a second time interval, different from the first time interval, sensing data at the sensor proximate to the radio frequency communication signals at the second sensor scan rate.

2. The method of claim 1, further comprising:
determining whether the radio frequency communication signals are active,
sensing sensor data at the sensor scan rate in accordance with a determination that the radio frequency communication signals are active; and
sensing sensor data at the second sensor scan rate in accordance with a determination that the radio frequency communication signals are inactive.

3. The method of claim 2, wherein determining whether the radio frequency communication signals are active comprises receiving a flag signal from a radio frequency circuitry located proximate to the sensor.

4. The method of claim 2, wherein determining whether the radio frequency communication signals are active comprises detecting a presence of communication frames in the radio frequency signals, the communication frames having an associated communication frame rate.

5. The method of claim 1, wherein:
an output of the sensor at the sensor scan rate while the radio frequency communication signals are active includes a first DC value based on the radio frequency communication signals;
an output of the sensor at the second sensor scan rate while the radio frequency communication signals are active includes a second DC value based on the radio frequency communication signals, the first DC value greater than the second DC value; and
a difference between the first DC value and the second DC value exists for a fixed signal strength of the radio frequency communication signals.

6. The method of claim 1, wherein the sensor scan rate is an integer multiple or integer sub-multiple of a communication frame rate of the radio frequency communication signals.

7. The method of claim 1, wherein generating the sensor scan rate synchronized with the radio frequency communication signals comprises receiving a frame timing signal or sub-frame timing signal from a radio frequency circuitry and scaling the received frame timing signal or sub-frame timing signal to a desired sensor scan rate frequency.

8. A non-transitory computer readable storage medium having stored thereon a set of instructions, that when executed by a processor causes the processor to:
generate a sensor scan rate synchronized with radio frequency communication signals transmitted proximate to a sensor;
while the radio frequency signals are being transmitted, sense data at the sensor proximate to the radio frequency communications signals at the sensor scan rate;
generate a second sensor scan rate based on a reference clock source, the second sensor scan rate being asynchronous to the communication frame rate; and
during a second time interval, sense data at the sensor proximate to the radio frequency communications signals at the second sensor scan rate.

9. The non-transitory computer readable store medium of claim 8, wherein the instructions further cause the processor to:
determine whether the radio frequency circuitry is operating,
sense sensor data at the sensor scan rate in accordance with a determination that a radio frequency circuitry transmitting the radio frequency communications signals is operating; and
sense sensor data at the second sensor scan rate in accordance with a determination that the radio frequency circuitry is not operating.

10. The non-transitory computer readable storage medium of claim 9, wherein determining whether the radio frequency communication signals are active comprises receiving a flag signal from the radio frequency circuitry located proximate to the sensor.

11. The non-transitory computer readable storage medium of claim 9, wherein determining whether the radio frequency communication signals are active comprises detecting a presence of communication frames in the radio frequency communication signals, the communication frames having an associated communication frame rate.

12. The non-transitory computer readable storage medium of claim 8, wherein:
an output of the sensor at the sensor scan rate while the radio frequency communication signals are active includes a first DC value based on the radio frequency communication signals;
an output of the sensor at the second sensor scan rate while the radio frequency communication signals are active includes a second DC value based on the radio frequency communication signals, the first DC value greater than the second DC value; and
a difference between the first DC value and the second DC value exists for a fixed signal strength of the radio frequency communication signals.

13. The non-transitory computer readable storage medium of claim 8, wherein the sensor scan rate is an integer multiple or integer sub-multiple of a communication frame rate of the radio frequency communication signals.

14. The non-transitory computer readable storage medium of claim 8, wherein generating the sensor scan rate synchronized with the radio frequency communication signals comprises receiving a frame timing signal or sub-frame timing signal from a radio frequency circuitry and scaling the received frame timing signal or sub-frame timing signal to a desired sensor scan rate frequency.

15. An electronic device comprising:
sensor circuitry configured to sense data at a scan rate;
a reference clock signal generator configured to generate a reference clock signal;
clock generation circuitry configured to generate the scan rate based on an input clock signal; and
clock selection circuitry configured to selectively couple the input clock signal to one of the reference clock signal and a frame rate reference signal, the frame rate reference signal synchronized with radio frequency communication signals transmitted proximate to the sensor circuitry.

16. The electronic device of claim 15, further comprising:
a light emitter;
wherein the sensor circuitry is configured to sense light transmitted by the light emitter and reflected by a user's skin.

17. The electronic device of claim 15, wherein the reference clock signal is asynchronous to a transmission frame rate of the radio frequency communication signals transmitted proximate to the sensor circuitry.

18. The electronic device of claim 15, further comprising second clock generation circuitry configured to generate the frame rate reference signal based on a frame rate or sub-frame rate of the radio frequency communication signals.

19. The electronic device of claim 15, wherein the clock selection circuitry is configured to:
   determine whether the radio frequency communication signals are active;
   couple the input clock signal to the frame rate reference signal in accordance with a determination that the radio frequency communication signals are active; and
   couple the input clock signal to the reference clock signal in accordance with a determination that the radio frequency communication signals are inactive.

20. The electronic device of claim 19, wherein determining whether the radio frequency communication signals are active comprises detecting a presence of communication frames in the radio frequency communication signals, the communication frames having an associated communication frame rate.

21. The electronic device of claim 19, wherein the sensor scan rate is an integer multiple or integer sub-multiple of a communication frame rate of the radio frequency communication signals when the clock selection circuitry couples the input clock signal to the frame rate reference signal.

* * * * *